United States Patent [19]

Caufield et al.

[11] Patent Number: 5,650,320

[45] Date of Patent: Jul. 22, 1997

[54] LANTHIONINE ANTIBIOTIC COMPOSITIONS AND METHODS

[75] Inventors: Page W. Caufield; Jan Novak, both of Birmingham, Ala.

[73] Assignee: University of Alabama at Birmingham Research Foundation, Birmingham, Ala.

[21] Appl. No.: 230,473

[22] Filed: Apr. 20, 1994

[51] Int. Cl.⁶ .............................. C12N 1/21; C12N 15/63; C07H 21/04
[52] U.S. Cl. .............................. 435/252.3; 435/320.1; 435/242.33; 435/253.4; 536/23.7
[58] Field of Search ..................... 536/23.7; 435/320.1, 435/252.3

[56] References Cited

U.S. PATENT DOCUMENTS

| | | | |
|---|---|---|---|
| 4,740,593 | 4/1988 | Gonzales et al. | 435/243 |
| 4,980,163 | 12/1990 | Blackburn et al. | 434/94.63 |
| 5,043,176 | 8/1991 | Bycroft et al. | 426/335 |
| 5,135,910 | 8/1992 | Blackburn et al. | 514/2 |

OTHER PUBLICATIONS

Caufield et al., "Distinct Bacteriocin Groups Correlate with Different Groups of Streptococcus mutans Plasmids," *Infection and Immunity*, 48(1):51–56, 1985.

Caufield et al., "Evidence That Mutacin II Production Is Not Mediated by a 5.6–kb Plasmid in Streptococcus mutans," *Plasmid*, 24:110–118, 1990.

Caufield et al., "Use of Transposon Tn916 to Inactivate and Isolate a Mutacin–Associated Gene from Streptococcus mutans" *Infection and Immunity*, 58(12):4126–4135, 1990.

Delisle, "Properties of mutacin b, an antibacterial substance produced by Streptococcus mutans strain BHT," *Microbios*, 46:21–28, 1986.

Kaletta and Entian, "Nisin, a Peptide Antibiotic: Cloning and Sequencing of the nisA Gene and Posttranslational Processing of Its Peptide Product," *Journal of Bacteriology*, 171(3):1597–1601, 1989.

Liu and Hansen, "Enhancement of the Chemical and Antimicrobial Properties of Subtilin by Site–directed Mutagenesis," *The Journal of Biological Chemistry*, 267(35):25078–25085, 1992.

Liu and Hensen, "Some Chemical and Physical Properties of Nisin, a Small–Protein Antibiotic Produced by Lactococcus lactis, " *Applied and Environmental Microbiology*, 56(8):2551–2558, 1990.

Loyola–Rodriguez et al., "Purification and properties of extracellular mutacin, a bacteriocin from Streptococcus sobrinus," *Journal of General Microbiology*, 138:269–274, 1992.

Mayer et al., "Isolation of Mutacins in Cell Free Extracts and Analyses of Some Physical and Biological Properties," *Rev. Microbiol*, 23(4):221–225, 1992.

Parrot et al., "Preliminary characterization of four bacteriocins from Streptococcus mutans," *Can. J. Microbiol.*, 36:123–130 1990.

Sevag et al., "The Isolation of the Components of Streptococcal Nucleoproteins in Serologically Active Form," *Journal of Biological Chemistry*, 124:425–436, 1938.

Novak, et al. "Isolation and Biochemical Characterization of a Novel Lantibiotic Mutacin from Streptococcus mutans," 176:4316–4320, 1994.

Novak, et al. "Genetic and Biochemical Characterization of a Novel Lantibiotic from Streptococcus Mutans," 7th International Congress of Bacteriology and Applied Microbiology Division, Jul 3–8, 1994.

Novak, et al, "Biochemical Analysis of a Group II Mutacin from Streptococcus mutans," 93rd General Meeting, Atlanta, Georgia, May, 1993.

Novak, et al, "Characterization of a Novel Lantibiotic from Streptococcus mutans," IVth International ASM Conference on Streptococcal Genetics, Santa Fe, New Mexico, May 15–18, 1994.

*Primary Examiner*—Robert A. Wax
*Assistant Examiner*—Kawai Lau
*Attorney, Agent, or Firm*—Benjamin Aaron Adler

[57] ABSTRACT

Certain bacteria indigenous to humans produce antimicrobial substances called bacteriocins which inhibit other bacteria, including members of their own species. Mutacins are a class of antibiotic substances made by Streptococcus mutans. Disclosed is the purification and biochemical characterization of a novel lanthionine-containing mutacin peptide from S. mutans. The purified peptide is pH- and temperature-stable and its amino acid composition indicates the presence of lanthionine and β-methyllanthionine. Also provided are methods of making and using the purified polypeptide.

7 Claims, 6 Drawing Sheets

LANTHIONINE ANTIBIOTIC COMPOSITIONS AND METHODS

The United States government owns rights in the present invention pursuant to grant NIDR:NIH DE 09082 from the National Institutes of Health.

BACKGROUND OF THE INVENTION

1. Field of the Invention

The invention relates to polypeptide antibiotics and to the identification of genetic loci associated with expression of the antibiotics. The invention particularly describes a purified lanthionine-containing antimicrobial agent and methods and compositions for treatments employing the antibiotic.

2. Description of Related Art

The phenotypically similar group of bacteria collectively known as the mutans streptococci are considered the major etiologic agents responsible for dental caries and have been implicated as major causative agents in certain infectious and transmissible diseases. The species most commonly associated with dental caries is *Streptococcus mutans*. Attempts to better understand the genetic determinants that contribute to the cariogenic potential of this organism, as well as its natural history as an agent of infectious disease, have only recently been explored. For example, a molecular approach has been employed to delineate the structure, function, and regulation of a number of different enzymes including the glucosyltransferases that are involved with sugar metabolism, an important virulence factor responsible for the metabolic conversion of sucrose to extracellular polymers to form critical mass and provide for fermentable substrates (Hamada, et al., 1986).

The other two major factors thought to be involved with the pathogenicity of *S. mutans* are its acidogenic/aciduric properties (Caufield, et al., 1990A) and its ability to elaborate poorly characterized bacteriocin-like substances, generally known as mutacins, which may provide a selective force necessary for sustained colonization in a milieu of densely packed competing organisms found in plaque (Buchman, et al., 1988). Collectively called "mutacins" these agents kill other bacteria of the same or closely related species. The mutacins are only similar in name and host producer, as the properties of those described in the literature differ widely. Mutacins associated with plasmid-containing strains of *S. mutans* have been designated as either Group I or II (mutacin I and mutacin II; (Gross and Morell, 1971). Therefore, the production of mutacins is one characteristic of *S. mutans* that appears to contribute to its ability to colonize and be sustained, particularly in the oral cavity. Mutacins thus may be considered virulence factors.

The mutans streptococci produce several different bacteriocin-like inhibitory substances, i.e., mutacins (Parrot, et al., 1989). To date, most remain only partially characterized (Hamada, et al., 1986; Loyola, et al., 1992). Reasons for limited success in characterization of these substances are likely to be that: 1) they are made in small quantities; 2) production occurs only under special cultivation conditions; 3) a lack of production in liquid media; and 4) difficulty in isolating these 'mutacins' from the media.

Bacteriocins are traditionally defined as proteinaceous substances capable of exerting lethal or bactericidal effects on other bacteria within the same species or against closely related species (Tagg, et al., 1976). Among the gram-positive bacteria, however, this definition becomes somewhat less precise because inhibitory substances exhibit a wider spectrum of activity. Moreover, bacteriocins are not always proteins and do not fit the traditional definition originally intended for the better studied gram-negative bacteriocins, e.g., colicin. Recent studies involving the molecular characterization and sequencing of several gram-positive bacterial inhibitory polypeptides, including nisin, epidermin, pep5 and subtilin, among others, reveal ribosomally translated, but posttranslationally processed peptides having modified amino acids and thioether linkages. Collectively, these polypeptide antibiotics are termed lantibiotics or lanthionine antibiotics (Allgaier, et al., 1986; Buchman, et al., 1988). It is now clear that mutacin II group belongs to the lanthionine family of antibiotics.

A few characteristics of certain mutacins have been determined. "Mutacin" activity appears to be associated with the presence of a 5.6 kb plasmid in *S. mutans*; however mutacin production in plasmid-containing strains of mutans streptococci is not plasmid-encoded (Caufield, et al., 1990A). Among strains of *S. mutans* harboring a 5.6 kb plasmid, at least two distinct, but closely related mutacin producing/immunity groups exist (Parrot, et al., 1990). Efforts have consequently focused on locating and characterizing the chromosomal locus responsible for mutacin expression. Initial attempts to identify the gene(s) responsible for mutacin expression employed transpositional mutagenesis using transposon Tn916 as the mutagen (Caufield, et at., 1990B). Five different chromosomal loci associated with mutacin expression have been identified.

Unfortunately, very little is known about the many described extracts with "mutacin" activity, such as their composition and under what conditions they are made. Because the compositions investigated were made in small quantities and only under certain poorly defined conditions, past attempts to partially isolate and biochemically characterize "mutacins" have yielded a wide array of results. Results of studies conducted to date, primarily using crude cell-free extracts, have led to the description of mutacins with different molecular weights and differential sensitivity to pH and digestive enzymes (Caufield, et al. (1985, 1990A, 1990B), Loyola-Rodriguez, et al. (1992), Delisle (1986), Pinto Alves, et al. (1992)). The relevance and usefulness of these results are particularly confounded by the lack of purity of the compositions.

A recognized need is the development of antimicrobials effective against a broad range of microorganisms. The present state of knowledge concerning mutacin-type antibiotics suggests that these compounds have potential as a class of antibacterials. However, owing to the lack of purity of the different mutacins and the inability to obtain such compounds in sufficient quantities, specific mutacins have yet to be clearly identified or developed for further use.

SUMMARY OF THE INVENTION

The present invention seeks to overcome these and other drawbacks inherent in the prior art by providing purified mutacin compositions and methods for the treatment of microbial infections in animals, including humans. The mutacin antimicrobials are isolated from *Streptococcus mutans* and show activity against several species of gram-positive bacteria. The invention also provides for the molecular cloning of the mutacin gene.

As used herein, "mutacin" is used to designate an antimicrobial agent isolatable from *S. mutans* and characterized by the properties as presented in this disclosure. These properties include an apparent molecular weight of about 2,500 Da as determined by HPLC-size exclusion chromatography, thermostability up to 100° C., resistance to a pH range of about 4–10, an isoelectric point of >8.4 and solubility in water-immiscible organic solvents. The term "isolatable from" as used herein, is intended to describe the various sources from which a mutacin in accordance with the present invention may be obtained. Appropriate sources are considered to be virtually all *S. mutans* species, with T8 and UA96 being particularly preferred, and also recombinant host cells engineered to express mutacin.

It is recognized that the literature describes impure compositions containing several mutacins elaborated by *S. mutans* and related species. However these "mutacin" containing compositions are different from the mutacin described herein in several important respects, including physical and biological properties, in addition to the significant factor of their purification.

The first area of disparity is in the predicted molecular weight characteristics of "mutacins". Parrot et al. (1990) describe four "mutacin extracts" with $M_r$'s ranging in the about 3500 Da to <12,000 Da as measured by dialysis, while Delisle (1986) describes a mutacin with an $M_r$ of between 3500 and 6000 Da also by dialysis, and Loyola-Rodriguez (1992) demonstrates a molecular weight of 6500 Da by SDS-PAGE electrophoresis.

Another area of significant disparity in the mutacin field relates to the relative purity of the samples tested. Crude bacterial extracts or supernatants have been described by Pinto-Alves (1992), Parrot (1990), and Delisle (1986) to contain "mutacin" activity. These crude preparations differentially inhibited the growth of gram-positive bacteria, however, the exact component(s) responsible for this activity are unknown. Loyola-Rodriguez, et al. have shown a somewhat purified "mutacin" from *S. sobrinus* isolated through a series of chromatographic steps and having an Mr of 6500 Da as measured by SDS-PAGE. However, this relatively purified mutacin did not exhibit bacteriocidal activity against *Actinomyces sp., Staphylococcus sp., Lactobaccilus sp.,* or *Escherichia coli.*

Since the original description of a "mutacin" over 10 years ago, a purified mutacin from *S. mutans* has eluded production, purification, and sequencing. Although some preliminary characterization of mutacins has been reported, the present invention describes for the first time the ability to produce a *Streptococcus mutans* mutacin in liquid culture. Also disclosed are advantageous methods for purifying mutacin in sufficient quantities to enable characterization of its biochemical properties and, indeed, in enough purity for protein sequencing.

The term "purified mutacin" as used herein, is intended to refer to a protein composition, isolatable from *S. mutans*, such as T8 and UA96, wherein the mutacin is purified to a substantial degree relative to its naturally-obtainable state, i.e., in this case, relative to its purity within a bacterial extract or growth supernatant. A purified mutacin therefore also refers to a mutacin polypeptide, significantly free from the environment in which it naturally occurs.

Generally, "purified" will refer to a composition which has been subjected to fractionation to remove several non-antimicrobial components, and which composition substantially retains its bactericidal or bacteriostatic activity. Purified, in this sense, usually refers to a composition in which the mutacin forms the major component of the composition, such as constituting about 90% of the proteins in the composition or more. The purified mutacin will typically be purified about 60- or 84-fold, i.e., to such a degree so that it has a specific activity of about 110,000 bacteriocidal units per milligram of total protein (BU/mg), or preferably, between about 110,000 and 150,000 BU/mg, and most preferably it will have a specific activity of about 150,000 BU/mg.

The isolated antimicrobial mutacin polypeptides of the invention are generally characterized as having substantial bacteriocidal activity. As used herein the term "substantial bacteriocidal activity" describes significant mutacin-directed bacterial cytolysis, as measured by any one of a variety of assays. Bacteriocidal activity may be advantageously examined and quantified by the deferred antagonism technique on trypticase soy-yeast agar (TSAY) using *S. sobrinus* OMZ176 or *S. sanguis* Ny101 as sensitive indicators (Parrot, et al., 1990). A unit of bacteriocidal activity (BU), present in liquid culture, is described as the lowest titer yielding a clear lytic-like zone of inhibition having clear edges and greater than 10 mm in diameter.

In certain embodiments, purified mutacin may be characterized as being the predominant band on an SDS-PAGE gel as detected, e.g., silver staining. Most preferably, the purified mutacin will be the only band detected on an SDS-PAGE gel stained with either Coomassie blue or silver stain, according to the amount to be detected.

The mutacins of the present invention have an apparent $M_r$ of about 2,500 Da as determined by high performance liquid chromatography using a size-exclusion column. This is a useful defining parameter which may be determined using the routinely employed technique of column chromatography. However, the highly purified mutacins may be found to have a slightly different exact $M_r$s, such as the molecular weight of 3,244.64±1.15 Da determined by ion spray mass spectroscopy for the T8-derived mutacin as determined from the m/z values, wherein z is equal to 2, 3, or 4 for m/z# 1623, 1083 and 812, respectively (see FIG. 4). Furthermore, the mutacin is thermostable, as measured by, e.g., incubating an agar plug at 100° C. for 30 minutes and quantitating bacteriocidal activity. The mutacin is stable over a pH range of 4–10, as measured by incubating the purified mutacin for 24 hours in appropriate 0.1M buffers, e.g., such as acetate, phosphate or glycine buffers, at room temperature, and tested for bacteriocidal activity. The mutacin has an isoelectric focusing point of >8.4 and is soluble in 70% ethanol, 8M urea (such as 70% ethanol or 8M urea), and guanidine-water solutions.

The mutacin has the following composition of amino acids per molecule: Arg$_2$, Asp$_2$, Glu$_3$, Gly, His, Ile, Lys, Met, Pro, Trp$_2$, Tyr, Val$_3$, Xaa$_2$, Yaa; wherein Xaa represents lanthionine and Yaa represents β-methyllanthionine. The mutacins of the invention may also be characterized by the presence of certain sequences. For example, by including the N-terminal sequence Asn Arg Trp Trp Gln Gly Val Val (SEQ ID NO:1), or by including an internal sequence Met Asn Xaa Xaa Trp His Xaa (SEQ ID NO:2).

The development of a growth medium which permits the purification of mutacin from liquid culture is an important factor to the invention. Chemically defined media (van der Rijn et al. (1980)) supplemented with yeast extract and soy bean trypticase are the preferred media for use in connection with mutacin purification. Accordingly where the term, growing a culture of a bacteria that produces the polypeptide, is used, this preferably means growing or culturing the bacteria in media comprising a chemically defined media supplemented with yeast extract and soy bean trypticase.

The mutacin polypeptides of the present invention may also be characterized as being isolatable by a method employing ultrafiltration and selective precipitation. More specifically, mutacin polypeptides may be isolated by a process including the steps of: growing a culture of a bacteria that produces the polypeptide; filtering the culture through a porous membrane filter and collecting the flowthrough; sequentially passing the flowthrough through ultra filtration membranes; collecting and retaining the filtrate of the final ultrafiltration step; mixing the retained filtrate with a water-immiscible organic solvent, such as benzene, ether, chloroform, ethyl acetate, methylene chloride, carbon tetrachloride, or chloroform, thereby forming a precipitate; washing the precipitate thus formed and solubilizing the precipitate using a chaotropic agent, such as guanidine, guanidinium or urea.

To prepare purified mutacin in accordance with the most preferred method of the present invention, one would first grow T8 S. mutans in supplemented growth media and then separate insoluble bacterial debry through a porous membrane, preferably a 0.45 µm diameter porous membrane. The collected flowthrough would be further subjected to sequential ultrafiltration through membranes with molecular weight cut-offs of, e.g., 100-, 10-, and 1-kDa. The retained filtrate of the final ultrafiltration step is collected and a precipitate is formed by mixing this final filtrate with a water immiscible organic solvent, and the solvent evaporated. The water immiscible organic solvent will preferably be chloroform. The precipitate is then washed with water or an aqueous buffer such as phosphate buffered saline, the like. The precipitate is solubilized with a chaotropic agent, such as guanidine, guanidinium, or urea, with 8M urea being most preferred. The dissolved mutacin-chaotrope mixture is finally precipitated with 20 volumes of water.

The substantially purified mutacin polypeptides having bacteriocidal activity against gram-positive bacteria, as exemplified by exhibiting bacteriocidal activity against members of the Actinomyces, Bacillus, Clostridium, Mycobacterium, Staphylococcus or Streptococcus species.

The polypeptide may also be purified by solvent-based thin-layer chromatography on TLC-coated Silicagel developed with a solvent comprised of methanol:water (7:3). The polypeptide containing portion may be detected by UV and the presence of mutacin antimicrobial activity confirmed using a biological sensitivity assay.

In a preferred embodiment the mutacin is purified from the supernatant or bacterial extract of Streptococcus mutans bacteria. In a more preferred embodiment the Streptococcus mutans bacteria is of the UA96 or T8 strain. In an alternative embodiment the polypeptide may be purified from a recombinant host cell which incorporates DNA, such as an expression vector, which encodes the mutacin. A preferred host cell for use in this regard is E. coli, with an E. coli strain that is recA being more preferred.

Various methods for quantifying the degree of purification of the mutacin will be known to those of skill in the art in light of the present disclosure. These include, for example, determining the specific activity of an active fraction, or assessing the relative purity of the polypeptide within a fraction by SDS/PAGE analysis. One preferred method for assessing the purity of a mutacin fraction is to calculate the specific activity of the fraction, to compare it to the specific activity of the initial bacterial extract, and to thus calculate the degree of purity, herein assessed by a "-fold purification number".

The actual units used to represent the amount inhibitory activity will, of course, be dependent upon the particular assay technique chosen to follow the purification. The present inventors prefer to use an assay based upon the deferred antagonism technique. One unit of activity in the assay used herein is defined as the lowest titer of activity that yields a lytic-like zone of inhibition having clear edges and being greater than 10 mm in diameter. However, using other assays, the definition of a unit of activity would naturally vary.

As is generally known in the art, to determine the specific activity, one would calculate the number of units of activity per milligram of total protein. In the purification procedure, the specific activity of the starting material, i.e., of the bacterial extract, would represent the specific activity of the mutacin in its natural state. At each step, one would generally expect the specific activity of the mutacin to increase above this value, as it is purified relative to its natural state. The use of "fold purification" is advantageous as the purity of an antimicrobial fraction can thus be compared to another despite any differences which may exist in the actual units of activity or specific activity.

It is contemplated that the antimicrobial mutacin of the present invention will preferably exhibit a specific activity of about 100,000 or 110,000 BU/mg, and may be purified up to a level of about 150,187 BU/mg of total protein. More preferably, the mutacins are particularly characterized as those being between about 60-fold purified and about 84-fold purified, with respect to the starting composition.

The most preferred method for purifying mutacin is that of filtration and organic solvent precipitation, however, various techniques suitable for use in protein purification are well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques.

The preferred purification method disclosed herein above contains several steps and represents the best mode presently known by the inventors to prepare a substantially purified mutacin. This method is currently preferred as it results in the substantial purification of the mutacin, as assessed by deferred antagonism, in yields sufficient for further characterization and use. This preferred mode of mutacin polypeptide purification involves the execution of certain purification steps in the order described herein. However, as is generally known in the art, it is believed that the order of conducting the various purification steps may be changed, or that certain steps may be omitted, and still result in a suitable method for the preparation of a substantially purified antimicrobial mutacin polypeptide.

As mentioned above, although preferred for use in certain embodiments, there is no general requirement that the mutacin always be provided in their most purified state. Indeed, it is contemplated that less substantially purified mutacin, which are nonetheless substantially enriched in antimicrobial activity relative to the natural state, will have utility in certain embodiments. These embodiments include using the mutacin as a diagnostic test for S. mutans subtypes. Serologic reagents developed against the mutacin may also be used to rapidly identify and define mutacin subtypes. Partially purified mutacin polypeptide fractions for use in such embodiments may be obtained by subjecting a bacterial extract to one or a combination of the steps described above.

Using the present purification procedures the inventors have produced and purified mutacin from two strains of S. mutans: T8 and UA96. Although similar in their basic characteristics such as molecular weight, resistance to heat and pH, and solubility in water immiscible organic solvents, minor differences in the mutacin have been noted between these two closely related strains. For example, the mutacins exhibit different migration patterns on TLC. Using a degenerate oligonucleotide complementary to the amino terminal mutacin protein sequence polymorphisms are apparent in Southern hybridization patterns. These minor differences are also clear using arbitrary primer-PCR fingerprinting. Finally, the mutacin derived from the S. mutans T8 strain was more amenable to purification which allowed the determination of molecular weight by mass spectroscopy and protein sequencing. Naturally it will understood by those of skill in the art that mutacins with such variations as these, which nevertheless have the general properties described forthwith fall within the scope of the present invention.

Further compositions of the invention include pharmaceutical composition comprising substantially purified mutacin polypeptides dispersed in pharmacologically acceptable carriers. The admixture consisting essentially of a therapeutically effective amount of the mutacin polypeptide in a pharmacologically acceptable carrier. These carriers may be incorporated with excipients and used in the form of, e.g., mouthwashes, dentifrices, assimilable edible carriers, tablets, buccal tables, trouches, capsules, elixirs, wafers, suspensions, syrups, and the like as disclosed herein, and by means well known by those of skill in the art. The mutacin may also be incorporated into pharmacologically acceptable carriers for parenteral delivery, such as suspensions used for intravenous, intramuscular and subcutaneous injection. The phrase "pharmaceutically acceptable" refers to molecular entities and compositions that do not produce an allergic or similar untoward reaction when administered to a human.

The preparation of an aqueous composition that contains a mutacin as an active ingredient will be well understood to those of skill in the art in light of the present disclosure. Typically, such compositions may be prepared as injectables, either as liquid solutions or suspensions; solid forms suitable for solution in, or suspension in, liquid prior to injection can also be prepared. The preparation can also be emulsified.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule. Techniques such as these would also, of course, be appropriate for the production of the mutacin polypeptides in accordance with the present invention.

A first step in such cloning procedures is the screening of an appropriate DNA library, such as, in the present case, an S. mutans-derived library. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. Another cloning approach contemplated to be particularly suitable is the use of a probe or primer directed to a gene known to be generally associated with, e.g., within the same operon as, the structural gene that one desires to clone. For example, in the case of mutacin, one may wish to use a primer directed to the conserved ABC transporter genes that are known to be associated with all lanthionine antibiotic genes.

After identifying an appropriate DNA molecule by any or a combination of means as described above, the DNA may be then inserted into any one of the many vectors currently known in the art and transferred to a prokaryotic or eukaryotic host cell where it will direct the expression and production of the so-called "recombinant" version of the protein. The recombinant host cell may be selected from a group consisting of S. mutans, E. coli, S. cerevisae, Bacillus sp., Lactococci sp., Enterococci sp., or Salmonella sp. In certain preferred embodiments, the recombinant host cell will have a recA phenotype.

It will be understood that recombinant mutacin may differ from naturally-produced mutacin in certain ways. In particular, the degree of post-translational modifications, such as, for example, glycosylation and phosphorylation may be different between the recombinant mutacin and the mutacin polypeptide purified from a natural source, such as S. mutans T8 or UA96.

In still another embodiment, the present disclosure provides methods for cloning the DNA encoding the mutacin polypeptide. Using methods well known to those of skill in the art, the DNA that encodes the purified S. mutans mutacin of the present invention may be isolated and purified. For example, by designing a degenerate oligonucleotide comprising nucleotides complementary to the peptide sequences (SEQ ID NO:1 and 2) the mutacin encoding DNA can be cloned from an S. mutans genomic DNA library.

The DNA sequences disclosed by the invention allow for the preparation of relatively short DNA (or RNA) sequences which have the ability to specifically hybridize to S. mutans gene sequences encoding the present antibiotic, termed mutA. The term mutA as used herein is meant to describe the gene locus encoding the mutacin structural gene. In these aspects, nucleic acid probes of an appropriate length are prepared. Such probes are typically prepared based on the consideration of the defined amino acid sequences of purified mutacin. The ability of such nucleic acid probes to specifically hybridize to the S. mutans mutA gene sequences lend them particular utility in a variety of embodiments. For example, the probes may be used in a variety of diagnostic assays for detecting the presence of S. mutans organisms in a sample, for example, a saliva sample from the oral cavity. However, other uses are envisioned, including identification and isolation of mutA gene sequences encoding similar or mutant polypeptides related to the mutacin. Other uses include the use of mutant species primers or primers to prepare other genetic constructs.

In further embodiments, the DNA encoding the mutacin of the present invention allows for the large scale production and isolation of the mutacin polypeptide. This can be accomplished by directing the expression of the mutacin polypeptide by cloning the DNA encoding the mutacin polypeptide into a suitable expression vector. Such an expression vector may then be transformed into a host cell that is able to produce the mutacin protein. The mutacin protein may then be purified, e.g., by means provided for in this disclosure and utilized in a biologically active form. Non-biologically active recombinant mutacin may also have utility, e.g., as an immunogen to prepare anti-mutacin antibodies.

Another approach toward identifying the gene(s) responsible for the production of mutacin is to locate genes known to be adjacent to the mutacin structural gene. From sequenced lantibiotic gene loci, it is clear that several processing and export enzymes are highly conserved among the lantibiotic producers and share areas of common sequences. For example, all the known lantibiotic producers have so-called ABC transporter genes responsible for making a protein involved with mutacin export. A series of oligonucleotide primers complementary to conserved sequences could be used in PCR reactions to amplify the intervening sequence, this amplicon could be used as a probe to identify the ABC transporter gene (PCR technology is described in U.S. Pat. No. 4,603,102, incorporated herein by reference). Since the ABC transporter gene is part of every known lantibiotic loci described thus far, the structural gene for mutacin should be nearby and readily identified by so called "chromosome walking".

Methodological aspects of the invention include methods for contacting gram-positive bacteria with the mutacin polypeptides, thereby killing the bacteria. The term "contacting gram-positive bacteria" as used herein, is meant to encompass the delivery of an amount of mutacin having a substantial bacteriocidal component. The "contact" process is the process by which the mutacin polypeptide comes in direct juxtaposition with the target cell. The term "target cell" as used herein, is a bacterial cell against which the present mutacin exhibits substantial bacteriocidal activity.

To contact mutacin polypeptides with the target cells with a mutacin-containing composition one may simply add the polypeptides or composition to potential bacterial targets in vitro. Alternatively, one may administer a biologically effective amount of a pharmacologically acceptable form of the mutacin polypeptides or composition to an animal, where it will contact target cells in a biological fluid in vivo. In this context, "contact" is achieved simply by administering the composition to the animal.

Virtually any pharmaceutical polypeptide formulation may be used, including, but not limited to, formulations for parenteral administration, such as for intravenous, intramuscular and subcutaneous administration; inhalants, aerosols and spray formulations; formulations of peptides for topical use, such as in creams, ointments, dentifrices, powders, and gels; polypeptides encapsulated in micelles or liposomes and drug release capsules including the active peptides incorporated within a biocompatible coating designed for slow-release; and mouthwashes and other buccal washes.

In final preferred embodiment, a pharmacological composition containing the mutacin protein of the present disclosure may be used for the treatment of dental caries. The treatment comprising orally administering a therapeutically effective amount of the mutacin polypeptide in a pharmacologically acceptable carrier. In another embodiment the polypeptide is administered topically. The mutacin polypeptides may be used for preventing or inhibiting development of dental caries by administering to an individual having or susceptible to dental caries a therapeutically effective amount of a composition comprising the mutacin polypeptide in a pharmacologically acceptable carrier.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
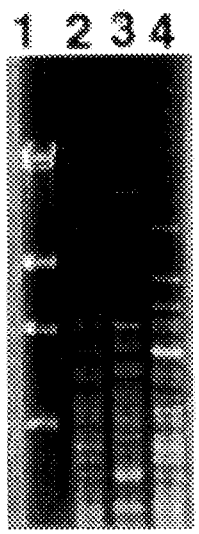
FIG. 1 is a Restriction length polymorphisms of T8 (lane 2), UA140 (lane 3), and UA96 (lane 4). Total DNA was isolated and cut with HaeIII. Lane 1 is a lambda/HindIII size standard.

A review of the literature concerning lantibiotics and other bacteriocin-like substances supports two main themes. One, there appears to be as many antibiotic substances as there are species. Even within the same species, several different antibiotics can be distinguished. Even though many of these substances exhibit similar properties (phenotypes), their genetic components (genotypes) may differ. Second, in every lantibiotic system characterized genetically thus far, and without exception, each locus consists of multiple genes arranged as contiguous coding sequences and in many cases, coordinately regulated. The genes and their products involved in mutacin expression are likely to lie within a cluster, making identification and transfer of the complete system to a non-producer strain feasible.

The present application describes the isolation and characterization of a lanthionine-containing antibiotic (lantibiotic) from human-derived strains of *S. mutans*. The lantibiotic will be referred to herein as "mutacin" with the understanding that other mutacin-like antibacterials are associated with various Streptococcus strains. Lantibiotics are polycyclic peptides with several intrachain sulfide bridges, consisting of the thioether amino acids lanthionine and β-methyllanthionine (Jung, 1991). In addition, lantibiotics contain a β-unsaturated amino acids such as didehydroalanine and didehydroaminobutyric acid, posttranslationally modified via dehydration of serine and threonine residues (Dodd, et al., 1990). The dehydrated, unsaturated serine or threonine residues can remain as such or form thioether bridges with neighboring cysteine.

Perhaps the best studied, and clearly the oldest known polypeptide antibiotic is nisin (Hurst, 1981). Produced by *Lactococcus lactis*, nisin is widely used in European countries as a food preservative. More recently, nisin has been tested as an anti-plaque agent in beagle dogs (Howell, et al., 1993). Nisin is a 3.4 kDa peptide that exhibits a fairly narrow spectrum of activity mainly against gram-positive bacteria including most streptococci, staphylococci, clostridia including *C. botulinum*, and *Mycobacterium tuberculosis*, among others. Nisin is not effective against most gram-negative bacteria (neisseria is an exception), fungi or yeast (Hurst, 1981). Because of its unique cyclic thioether ring structure and small size, the nisin molecule is extremely heat stable, a property that enhances its suitability for the food industry. Sensitive to pancreatic enzymes such as trypsin and chymotrypsin, however, nisin is readily inactivated when ingested.

Nisin and other lantibiotics exert their antibacterial activity by interacting with cell membranes, resulting in a decrease of the membrane potential gradient with ensuing membrane depolarization, disruption and rupture leading to irreversible cell lysis (Sahl, 1991). For this reason, lantibiotics are bactericidal. As highly charged cationic peptides, the membrane active component of lantibiotics resides in its amphipathic amino acid composition, arranged into both hydrophobic and hydrophilic domains. In addition, the lantibiotics are preceded by a leader sequence arranged in an α-helical conformation, contributing to its amphipathic properties and putative function as an escort/processing "handle."

Other gene products necessary for posttranslational modification, cleavage, and export of nisin are known; their location, genetic determinants and some aspects of their regulation have been recently reported (Kaletta and Entian, 1989; van der Meer, et al., 1993). Recent data indicate that the coding sequence of the nisin structural gene is part of a much larger transcript, somewhere between 2 and 5 kb, indicating the nisin gene is part of a polycistronic cluster (Steen and Hansen, 1991). It has been shown that an insertion of a transposon such as Tn916 anywhere within this 2 to 5 kb transcript is likely to result in the inactivation of the nisin gene and yield a nisin negative phenotype.

Prior to its genetic characterization, nisin was thought to be non-ribosomally synthesized because it contained nonprotein amino acids including lanthionine and β-methyllanthione, among others. A complete understanding evolved after the amino acid sequence derived from the DNA sequence was compared with the actual amino acid sequence. In the place of expected serines and threonines were the lanthionine and β-methyllanthiones; other residues were apparently dehydrated it thus became clear that the mature nisin molecule was the result of posttranslational modifications, thereby prompting a search for these otherwise unknown processing enzymes began.

Functions ascribed to the gene products from the nisin cluster include the following; nisA, the structural gene coding the precursor of nisin; nisB, a membrane-located enzyme involved with processing; nisT, an ABC-translocator whose function includes the export of peptides; nisC, function unknown; nisI, a lipoprotein involved with immunity; nisP, a membrane-located serine protease; and nisR, a DNA binding protein involved with regulation of nisin expression (van der Meer, et al., 1993). Analogs to most of the nisin genes have been found within the subtilin locus (Schnell, et al., 1992) and the epidermin locus (Schnell, et al., 1992). It appears that Bac/Hly from *E. faecalis* may also be a member of the lantibiotic family as the A factor is a protease capable of not only activating the Bac molecule just prior to its export, but also serves as an "immunity" factor by proteolytic cleavage of incoming Bac from other Bac-producing cells. This dual role for the A component appears unique at the present but may turn out to be a common theme in other lantibiotic producers. The polycistronic nature of the Hly locus is reminiscent of the nisin cluster as recently presented by Booth and Gilmore (1993).

The entire locus of at least some of the lanthionine antibiotics can be transferred en bloc to a non-producer strain. This is true for nisin (Horn, et al., 1991), subtilin (Liu and Hansen, 1991), and epidermin (Schnell, et al., 1992). In fact, the plasmid-borne epidermin locus (14 kb) was recently expressed across species (Augustin, et al., 1992). In the case of nisin, transfer has evidently occurred in nature since the coding sequences were found on both large plasmids and on chromosomal sites. This observation was initially confusing, but clarified when it was found the nisin locus was a part of a transposon Tn5301 (Horn, et al., 1991) (Tn5276) along with the sucrose metabolism locus, sac. The relationship between nisin and the locus for sucrose catabolism is interesting. It is not known whether there is a parallel in *S. mutans* and mutacin, especially considering that sucrose metabolism is a major virulence factor in mutans streptococci.

The development of a growth medium which permitted the purification of mutacin from liquid culture was an important factor in the purification of the protein. Additional steps employing ultrafiltration and selective precipitation were critical to the purification process. A single, biologically active protein with an $M_r$ of 2,500 was the final product as measured by size exclusion high-performance liquid chromatography. Other distinct characteristics of the present purified mutacin are the molecular weight as determined by size exclusion HPLC and ion spray mass spectroscopy, trypsin, pH and temperature sensitivity, solubility in water-soluble solvents, and migration pattern on TLC. The temperature resistance, size, and biological activity found for purified mutacin are dissimilar to previously reported properties of other mutacins in situ in agar plates and as measured by thin-layer chromatography (Parrot, et al., 1990, and as summarized in Table 1).

TABLE 1

PHYSICO-CHEMICAL PROPERTIES OF PURIFIED MUTACIN

| PARAMETER | PROPERTY OF MUTACIN |
| --- | --- |
| Temperature | thermostable > 100° C. |
| Trypsin | sensitive |
| pH | stable pH 4 to 10 |
| Molecular weight 3.24 kDa (Mass spec) | ~2.5 kDa (from SDS-PAGE and HPLC) |
| pI | >8.4 (based on electrophoretic mobility |

TABLE 1-continued

PHYSICO-CHEMICAL PROPERTIES OF PURIFIED MUTACIN

| PARAMETER | PROPERTY OF MUTACIN |
|---|---|
| N-terminal sequence | 5 basic amino acids |
| Solubility | ethanol, urea, guanidine-water solution, slightly soluble in water. |

Based on its amino acid composition and isoelectric focusing point, mutacin demonstrates characteristics of a basic protein. This is consistent with its mobility in agar gels as detected by gel overlay with a sensitive indicator strain.

The present polypeptide contains lanthionine and most likely contains a related amino acid, β-methyllanthionine, as well. All data taken together indicate that the new group II mutacin is a member of the lanthionine-containing polypeptide family. Other lanthionine-containing peptides produced by gram-positive species include nisin from *Lactococcus lactis*, epidermin from *Staphylococcus epidermidis* and subtilin from *Bacillus subtilis* (Allgaier, et al., 1985; Gross and Kiltz, 1973; Gross and Morell, 1971).

The N-terminal amino acid sequence (Asn Arg Trp Trp Gln Gly Val Val) (SEQ ID NO:1) of mutacin as determined by Edman degradation was compared with known sequences in protein databases and found to be unique. Additional cycles did not reveal any PTH-amino acid derivatives. Both lanthionine and methyllanthionine are expected to be suitable for cleavage from protein with the Edman procedure. However, they were not detected as bis-PTH derivatives, apparently because of their low solubility compared to mono-amino acid derivatives. Edman cleavage of one residue contributing to lanthionine or methyllanthionine is expected to result in a blank cycle but sequencing should continue uninterrupted. It is possible that additional modifications of mutacin may explain the failure to remove further amino acids. The absence of methionine at the N-terminus suggests that mutacin is processed from a precursor form, as reported for other lantibiotics (Buchman, et at., 1988; Kaletta, et al., 1989; van der Meer, et al., 1993).

Biologically Functional Equivalents

Modifications and changes may be made in the structure of the mutacin compositions of the present invention and still obtain molecules having like or otherwise desirable characteristics. For example, it is well known in the art that certain amino acids may be substituted for other amino acids in a protein structure without appreciable loss of interactive binding capacity with structures such as, for example, bacteria, components of the immune system, and the like. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of mutacin proteins or peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where the mutacin polypeptides are concerned, it is contemplated that only about one to three, or more preferably, one or two, amino acids may be changed within a given peptide. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. In the present invention, for example, one will likely not choose to change the lanthionine or β-methyllanthionine residues which are particularly characteristic of this type of antibiotic.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is known that certain amino acids may be substituted for other amino acids having a similar hydropathic index or score and still result in a protein with similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant protein, which in turn defines the interaction of the protein with other molecules, including substrates, receptors, and cellular entities such as bacteria. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids is also made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e., with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Epitopic Core Regions

U.S. Pat. No. 4,554,101 (Hopp, incorporated herein by reference) also teaches the identification and preparation of epitopes from primary amino acid sequences on the basis of hydrophilicity. Through the methods disclosed in Hopp, one of skill in the art would be able to identify epitopes from within an amino acid sequence such as the mutacin sequences disclosed herein and those sequences obtained by cloning according to the methodology set forth in the present disclosure. The regions of sequence thus identified are also referred to as "epitopic core regions".

Numerous scientific publications have been devoted to the prediction of secondary structure, and to the identification of epitopes, from analyses of amino acid sequences (Chou & Fasman, 1974a,b; 1978a,b, 1979). Any of these may be used, if desired, to supplement the teachings of Hopp in U.S. Pat. No. 4,554,101. Moreover, computer programs are currently available to assist with predicting antigenic portions and epitopic core regions of proteins. Examples include those programs based upon the Jameson-Wolf analysis (Jameson & Wolf 1988; Wolf et al., 1988), and also, more recently, new programs for protein tertiary structure prediction (Fetrow & Bryant, 1993).

Nucleic Acid Hybridization

DNA sequences derived from the N-terminal amino acid sequence (SEQ ID NO:1) disclosed herein, and functional equivalents thereof, have particular utility as probes and primers in nucleic acid hybridization embodiments. As such, it is contemplated that oligonucleotide fragments corresponding to such sequences for stretches of between about 10 nucleotides to about 20 or so nucleotides will find particular utility. Oligonucleotides with other 10 or 20 or so nucleotide long sequences which correspond to the amino sequences set forth in SEQ ID NO:1 and SEQ ID NO:2, therefore, have particularly utility.

The ability of such nucleic acid probes to specifically hybridize to mutacin-encoding sequences will enable them to be of great use in, for example, detecting the presence of complementary sequences in a given sample. For example, the gene encoding the mutacin may be cloned and sequenced using the complementary nucleotide probes as disclosed herein. Furthermore, the area immediately surrounding the structural gene for mutacin may be characterized to identify regulatory regions and other genes related to the regulation, production, and processing of the mutacin polypeptide. However, other uses are envisioned, including the use of the sequence information for the preparation of mutant species primers, or primers for use in preparing other genetic constructions. This is particularly important in the preparation of second generation mutacin products, as described herein.

Nucleic acid molecules having stretches of 10, 15 or 20 or so nucleotides designed from a consideration of the amino acid sequences disclosed herein will have utility as hybridization probes for use in Southern and Northern blotting in connection with analyzing mutacin-like structural or regulatory genes in other organisms and in various bacterial strains. The total size of fragment, as well as the size of the complementary stretch(es), will ultimately depend on the intended use or application of the particular nucleic acid segment. Smaller fragments will generally find use in such hybridization embodiments.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of mutacin genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and\or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating mutacin genes.

Of course, for some applications, for example, where one desires to prepare engineered, i.e., intelligently designed, second generation mutacin products, e.g., by site-specific mutagenesis, or where one seeks to isolate mutacin-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, mutacin-hybridization conditions can be readily manipulated, according to the results desired.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator-substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to-specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of mutacin and mutacin peptides. The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a mutacin-encoding or mutacin peptide-encoding nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

As discussed above, it will be understood that this invention is not limited to the particular nucleic acid and amino acid sequences of SEQ ID NOS:1–2. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, mutacin proteins or peptides, including second generation mutacin variants, may be created via the application of recombinant DNA technology, in which changes in the protein structure are engineered, based on considerations of the properties of the amino acids being exchanged.

DNA segments encoding a mutacin gene may be introduced into recombinant host cells and employed for expressing a mutacin protein or peptide. Alternatively, through the application of genetic engineering techniques, subportions or derivatives of selected mutacin genes may be employed. Equally, through the application of site-directed mutagenesis techniques, one may re-engineer DNA segments of the present invention to alter the coding sequence, e.g., to introduce improvements to the antibiotic actions of the resultant protein or to test such mutants in order to examine their structure-function relationships at the molecular level. Where desired, one may also prepare fusion peptides, e.g., where the mutacin coding regions are aligned within the same expression unit with other proteins or peptides having desired functions, such as for immunodetection purposes (e.g., enzyme label coding regions).

5 Pharmaceutical Compositions and Formulations

Pharmaceutical compositions comprising the disclosed mutacins may be orally administered, for example, with an inert diluent or with an assimilable edible carrier or they may be enclosed in hard or soft shell gelatin capsules or they may be compressed into tables or may be incorporated directly with the food of the diet.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The active compounds may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally, e.g., formulated for intravenous, intramuscular, or subcutaneous injection. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Mutacin Purification

The cultivation of mutacin-producing mutans streptococci in a supplemented liquid media was an important step in the recovery of mutacin from liquid culture. Improved results were obtained in chemically defined media supplemented with yeast extract and soy bean trypticase. The protein antibiotic was isolated by chloroform extraction in a manner similar to that employed in isolation procedures for nisin (Sevag, et al., 1938). This was rather surprising, because the primary sequence of the nisin polypeptide is very different (Kaletta, et at., 1989). The mutacin protein obtained as in Example 1 was purified and its composition and properties determined.

Bacterial strains, plasmids and media. Bacterial strains and plasmids used are shown in Table 2.

TABLE 2

Bacterial strains and plasmids used.

| Strain | Plasmid | Relevant phenotype/genotype | Reference or Source |
|---|---|---|---|
| S. mutans | | | |
| UA96 | pUA96 | $Bac^{II+}Imm^{II+}Com^+$ | a |
| T8 | none | $Bac^{II}Imm^{II+}Com^+$ | b |
| UA620-9 | pUA96 | $Bac^{II}Imm^{II+}Tc^r$ bac-1::Tn916 | a |
| E. coli | | | |
| UA946 | pPC313 | pVA838::bac-1 | a |

[a] Caufield, et al., 1990B
[b] Caufield, et al., 1990A

S. mutans T8 and UA96 elaborate a group II mutacin ($Bac^{II+}$). Strain UA620-9 contains single transposon Tn916 insertion within a genetic loci associated with mutacin production (bac-1::Tn916). The insert portion of pPC313 was derived from a Tn916-inactivated bac-1 cosmid construct from which Tn916 was excised (Caufield, 1990B). Construct pPC313 differs from pPC264 in orientation only; transformation of pPC264 or pPC313 into UA620-9 (bac-1) restores the mutacin phenotype. The type A lantibiotics (mutacin II polypeptides are most similar to this group) and the bacterial species that produce them are shown in Table 3.

TABLE 3

Partial list of Type A lantibiotics

| Lantibiotic | Producer species | Size (kDa) | # lanthionine/ methyl-lanth. |
|---|---|---|---|
| nisin | Lactococcus lactis | 3.4 | 5 |
| subtilin | Bacillus subtilis | 3.3 | 5 |
| epidermin | Staphylococcus epidermidis | 2.2 | 4 |
| pep5 | Staphylococcus epidermidis | 3.5 | 3 |
| streptococcin A-FF22 | Streptococcus pyogenes | 2.8 | 3 |
| mutacin II | Streptococcus mutans | 2.5 | 3 |

For the purpose of isolating mutacin from liquid culture, producers were grown in chemically defined medium (CDM; (40) supplemented with yeast extract (YE; Difco, Cockeysville, Md.) and trypticase soy broth (TSB; Difco). Preliminary activity assays showed that a 1:1 mixture (v/v) of CDM and TSB supplemented with 3% YE resulted in the optimal recovery of mutacin from liquid culture.

All strains were stored frozen in Todd-Hewitt broth with 30% glycerol at −70° C. until needed. Tn916-containing strains were grown on Todd-Hewitt agar supplemented with tetracycline (5 μg/ml).

Mutacin assay. Mutacin production was detected by deferred antagonism technique on trypticase soy-yeast agar (TSAY) using *S. sobrinus* OMZ176, *S. mutans* 10449, or *S. sanguis* Ny101 as sensitive indicators (Parrot, et al., 1990). Mutacin present in liquid culture was quantified by spotting 25 µl of 2-fold dilutions of mutacin in phosphate buffered saline (PBS) onto the surface of TSAY overlaid with indicator strain as described. Spots were allowed to dry for 1 h, then the plates were incubated anaerobically for 24 h. The lowest titer yielding a zone of inhibition having clear edges was defined as one bacteriocin unit (BU).

Mutacin purification. Ten milliliters of an overnight culture of strain T8 or UA96 were used to inoculate 2 L of CDM and SBT supplemented with 3% YE media and incubated anaerobically for 48 h without agitation in a 2 L flask. Cultures were then subjected to a series of filtration and ultrafiltration steps as follows: 1) cells were first removed from medium with a 0.45 µm membrane; 2) the filtrate was then passed through a series of ultrafiltration membranes with molecular weight cut-offs of 100-, 10- and 1-kDa, respectively (Minitan, Millipore, Bedford, Mass.). An equal volume of chloroform was added to the 1-kDa retentate. The emulsion formed between the aqueous and chloroform layers was dried and washed with PBS. The protein was solubilized in 8M urea and was precipitated by the addition of 20 volumes of water. Table 4 shows the specific activity, yield, degree of purification, and total activity during the purification procedure at different stages of isolation. The final preparation of mutacin was more than 84-fold purified and over 90% pure (based on amino acid analysis).

TABLE 4

Purification of mutacin.

| Purification stage | Total Activity (BU) | Total protein (mg) | Spec. activity (BU/mg) | Purification (-fold) | Yield (%) |
|---|---|---|---|---|---|
| 0.45 µm filtrate | 1,204,800 | 678 | 1,778 | 1.0 | 100 |
| 100 kDa ultrafiltrate | 1,184,000 | 629 | 1,882 | 1.1 | 98 |
| 10 kDa ultrafiltrate | 1,147,200 | 359 | 3,200 | 1.8 | 95 |
| 1 kDa retentate | 652,800 | 64 | 10,232 | 5.8 | 54 |
| Collection from chloroform emulsion | 901,120 | 8 | 111,249 | 62.5 | 75 |
| Water precipitate from 8 M urea | 901,120 | 6 | 150,187 | 84.5 | 75 |

EXAMPLE 2

Mutacin Characterization

Mutacin produced into the optimized medium was recovered in 10-kDa ultrafiltrate and 1-kDa retentate, indicating a $M_r$ between 10,000 and 1,000. Further characterization of mutacin was accomplished by HPLC (Miller, et at., 1991). Samples for HPLC were dissolved in 0.5M guanidine, 50 mM TrisHCl, pH 7.0, and chromatographed in tandemly arranged Bio-Sil SEC 125 columns (Bio-Rad laboratories, Melville, N.Y.). The column effluent was monitored at 220 nm and elution time was compared to elution times for standard set of peptide markers. Purified mutacin revealed a single peak with an $M_r$ of about 2,500 when compared to the elution pattern of standard proteins.

pH stability and sensitivity to trypsin. Purified mutacin was mixed with different 0.1M buffers in range pH 4–11 (sodium acetate pH 4–6; sodium phosphate pH 7–8; glycine-NaOH pH 8–11). After one or 24 h incubation at room temperature, residual mutacin activity was assayed using the spot test described above. Mutacin residual activity after incubation at pH 11 dropped to about 50% activity.

Sensitivity to trypsin (Sigma Chemical Co., St. Louis, Mo.) was determined according to the manufacturer's recommendation by incubating purified mutacin (4096 BU) in 50 µl of 50 mM sodium phosphate buffer pH 7.5 with trypsin (2 µg) at room temperature. Samples were analyzed for residual mutacin activity at various time intervals.

Mutacin was sensitive to trypsin. After 10 min incubation with the protease, no activity in sample was detected. Control samples without trypsin retained their full activity under identical conditions.

Thermal Stability. Mutacin was thermostable as analyzed by residual activity after incubation at 80° C. for 30 min, and by incubating at 100° C. in loading buffer.

Amino acid analysis and sequencing. Purified mutacin was hydrolyzed in 6N HCl and the resultant amino acids analyzed by reverse-phase HPLC after precolumn derivatization with a hydrophobic fluorescent reagent (Miller, et al., 1990). Lanthionine (Sigma Chemical Co., St. Louis, Mo.) was included in standard assays in addition to the common amino acids.

Sequencing of the desalted mutacin was done by automated Edman degradation on a gas-phase micro-sequencing system (model PI 2090E, Porton Instrument Inc., Tarzana, Calif.). The system was equipped with an on-line PTH-amino acid analyzer. Comparison of the mutacin N-terminal amino acid sequence with known sequences in protein databases (non-redundant Swiss Prot+PIR+Gen Pept+ GPUpdate) was made using Wisconsin Genetics Computer Group program (1991).

Mutacin sequencing. Sequencing of mutacin peptide revealed following N-terminal amino acid sequence (SEQ ID NO:1):

Asn Arg Trp Trp Gln Gly Val Val

No additional sequence was detected in the following cycles. Comparison of obtained N-terminal sequence with known amino acid sequences in protein databases failed to reveal any meaningful homology.

Sequencing of fragments from a tryptic digest of mutacin verified the N-terminus and also permitted determination of an additional internal amino acid sequence (SEQ ID NO:2) as follows:

N-Met Asn X X Trp His X where X represents blank cycles consistent with the presence of lanthionine or β-methyllanthionine residues.

Amino Acid Composition. The amino acid composition of mutacin is shown in Table 5. The method employed for analysis did not allow the detection of tryptophan. Two unique peaks were evident in the analysis. The chromatographic positions indicated their potential derivation from lanthionine and β-methyllanthionine. One of the peaks was subsequently identified as lanthionine by comparison with the elution position of authentic lanthionine derivatized with the standard reagent. The chromatographic position of the other peak was consistent with its identification as β-methyllanthionine since the later amino acid would be slightly more hydrophobic than lanthionine.

TABLE 5

Amino acid composition of mutacin

| Amino acid | Residues per molecule |
|---|---|
| Arginine | 2 |
| Aspartic Acid | 2 |
| Glutamic acid | 3 |
| Glycine | 1 |
| Histidine | 1 |
| Isoleucine | 1 |
| Lysine | 1 |
| Methionine | 1 |
| Proline | 1 |
| Tryptophan | 2[a] |
| Tyrosine | 1 |
| Valine | 3 |
| Lanthionine | 2 |
| β-methyl-lanthionine | 1 |
| Total | 22 |

[a]Deduced from peptide sequencing

Biological Activity. Mutacin exhibited strong biological activity against several species of microorganisms, shown in Table 6, and as determined by the deferred antagonism assay on trypticase soy-yeast agar plates. Biological activity may also be measured by overlaying thin layer chromatography or SDS-PAGE gels with an indicator strain.

TABLE 6

Sensitivity to Mutacin

| Bacterial Species | Sensitivity[a] |
|---|---|
| *Actinomyces viscosus* | S |
| *Bacillus subtilis* 1687 | S |
| *Clostridium sporogenes* (ATCC 19606) | S |
| *Mycobacterium phlei* | S |
| *Staphylococcus aureus* | SS |
| *Streptococcus faecalis* 78.4 | S |
| *Streptococcus faecium* | S |
| *Streptococcus lactis* | S |
| *Streptococcus mitis* | S |
| *Streptococcus mutans* GS-5 | S |
| *Streptococcus mutans* 130 | S |
| *Streptococcus mutans* 159 | S |
| *Streptococcus mutans* WT | S |
| *Streptococcus rattus* | S |
| *Streptococcus salivarius* | S |
| *Streptococcus sanguis* | S |
| *Streptococcus pyogenes* | S |
| *Streptococcus pneumoniae* | |

[a]S, sensitive (zone radius >2 mm); SS, zone radius >S

Figure 3:
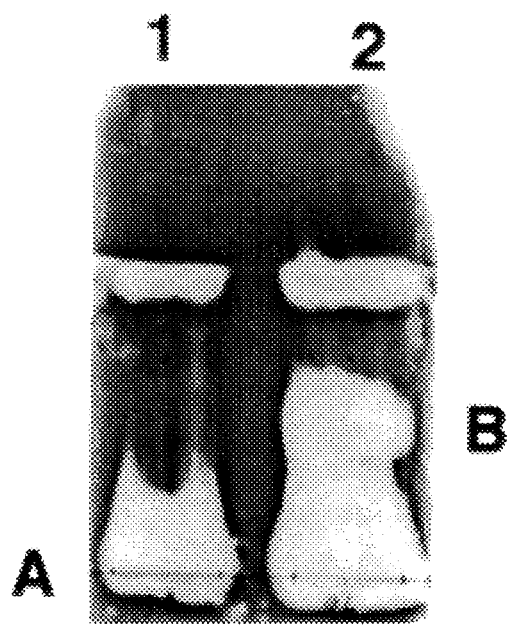
FIG. 3 shows TLC analysis of mutacin T8 (lane 1) and mutacin UA96 (lane 2). After separation, TLC plate was overlaid with the indicator strain and incubated 14 h anaerobically. Zone marked "A" is the main active zone in T8 (as also verified by MS), zone "B" is the active zone in UA96.

Thin layer chromatography. The mutacin T8 was also purified by solvent-based thin-layer chromatography (TLC) using TLC-coated Silicagel with UV indicator. The solvent used to develop the chromatography was a solvent comprising a mixture of 7:3 methanol water. The polypeptide portions may be detected by UV and the presence of anti-microbial activity confirmed using a biological activity assay as shown in FIG. 3.

Figure 4:
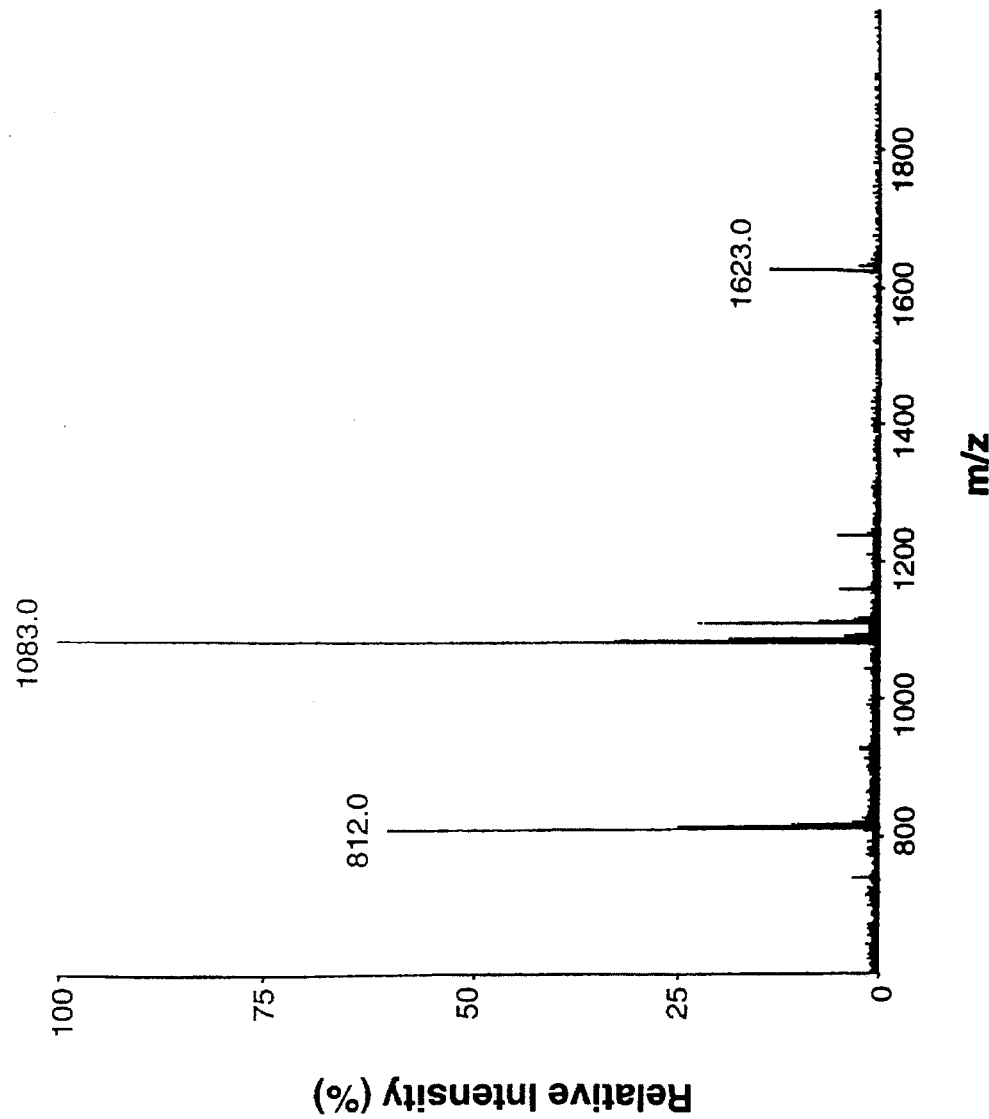
FIG. 4 shows ion spray mass spectrometric analysis of mutacin T8. The recorded multiple charged ions are consistent with MW estimate of 3,244.64±1.15 Da.

Mass Spectroscopy. Ion spray mass spectroscopy or spectrometry was performed on crude bacterial extracts and purified mutacin as shown (FIG. 4 shows purified preparation). The ion spray mass histogram shows the highest m/z value at 1623 with significant peaks at m/z of 1083 and 812, corresponding to z values of 2, 3, and 4 respectively. The molecular weight of purified mutacin T8 is therefore calculated as approximately 3,245. Partial MS-MS sequence analysis correlated with the N-terminal sequence found by Edman sequencing.

Figure 5A:
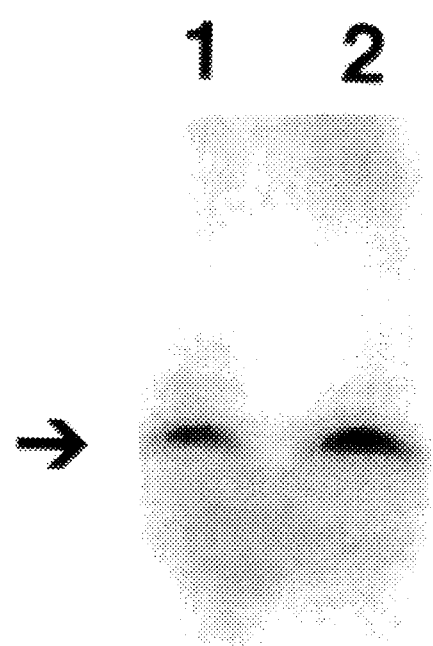
FIG. 5A purified mutacin T8 was separated on 10–20% linear gradient tricine gels. Tricine SDS-PAGE separates in the range of 1–100 kDa, and bands were detected by coomassie blue staining. Lane 1 samples were incubated with loading buffer at 40° C., and Lane 2 at 100° C., allowed to cool and loaded.
Figure 5B:
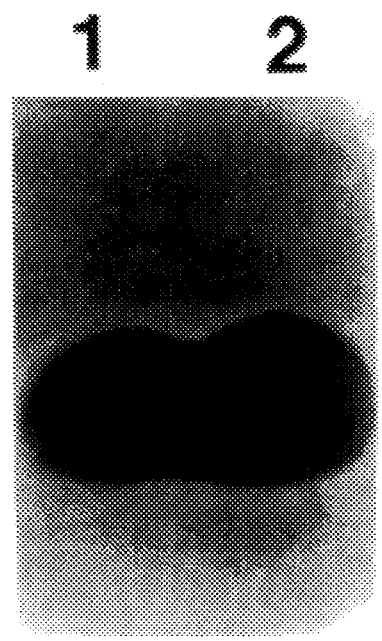
FIG. 5B the samples of FIG. 5A were incubated with loading buffer at 40° C. for 30 minutes, and 100° C., respectively, and cooled to room temperature before loading the gel. Biological activity was detected by overlay with *S. sanguis* Ny101 as the indicator strain.

SDS-PAGE electrophoresis. To further quantify the purity of the mutacin purified in the present invention the apparent molecular weight as determined by SDS/PAGE in the absence of reducing agents such as β-mercaptoethanol or dithiothreitol was determined. An approximate molecular weight of 2500 daltons was as observed as determined by SDS/PAGE in the presence of β-mercaptoethanol as demonstrated in FIG. 5A, as visualized by coomassie blue staining. Purified mutacin T8 was separated by SDS-PAGE on 10-20% linear gradient tricine gels and detected by coomassie blue staining. Biological activity was detected by overlay with *S. sanguis* Ny101 as the indicator strain (FIG. 5B).

However, it is, of course, generally understood by those of skill in the art that the migration of a polypeptide can vary with different conditions of SDS/PAGE (Capaldi et al., 1977) and with different sizing columns. It will therefore be appreciated that under differing electrophoretic and chromatographic conditions, the molecular weight assignments quoted above may vary.

It will be further understood that certain of the polypeptides may be present in quantities below the detection limits of the Coomassie brilliant blue staining or silver staining procedure as usually employed in the analysis of SDS/PAGE gels. Although not necessary to the routine practice of the present invention, it is contemplated that other detection techniques may be employed advantageously in the visualization of each of the polypeptides present within the growth factor. Immunologically-based techniques such as Western blotting using enzymatically-, radiolabel-, gold-, or fluorescently-tagged secondary antibodies are considered to be of particular use in this regard. An alternative means of detecting mutacin activity is to overlay the sample, such as SDS-PAGE separated mutacin, with an indicator strain *S. sanguis* Ny101, incubation, and measurement of the zone of inhibition.

EXAMPLE 3

Molecular Cloning of the Mutacin

The DNA sequences disclosed in the invention allow for the preparation of relatively short DNA (or RNA) sequences which have the ability to specifically hybridize to *S. mutans* gene sequences by preparing nucleic acid probes of an appropriate length. Such probes are typically prepared based on the consideration of the defined gene sequence of the mutacin gene or derived from flanking regions of this gene.

Figure 2:
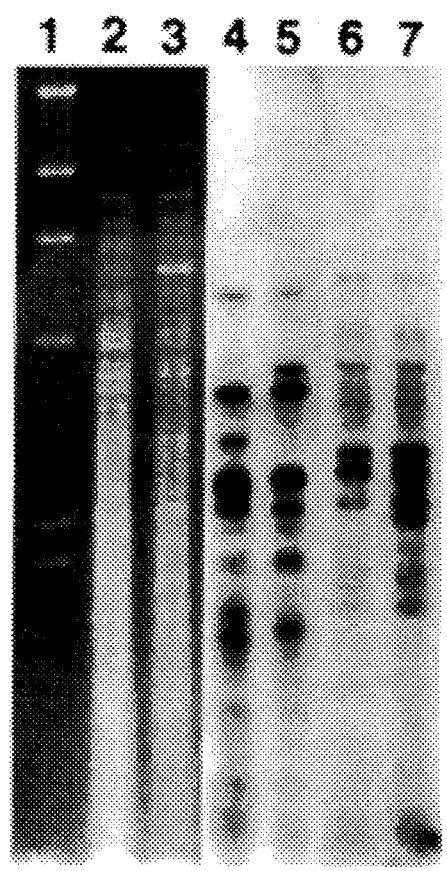
FIG. 2 is Southern hybridization of T8 (lanes 2, 4, 6) and UA96 (lanes 3, 5, 7) cut with various restrictions endonucleases (2 and 3 HaeIII; 4 and 5 PstI; 6 and 7 PstI/HindIII). Lane 1 is lambda/HindIII size standard. A degenerative 17-mer oligonucleotide designed according N-terminal amino acid sequence of mutacin T8 biotinylated at the 5' end was used as a probe, and developed by enhanced chemiluminescence.

DNA analysis and design of oligonucleotide probe. Suitable conditions for use in DNA isolation, restriction endonuclease analysis, Southern transfer and transformation are described in Caufield, et al., (1990B) and as described in, e.g., Sambrook, J., et al. Molecular Cloning: A Laboratory Manual, incorporated herein by reference. Degenerate oligonucleotide DNA probes are designed from the N-terminal amino acid sequence of isolated mutacin using the universal codon usage. Probes are radiolabeled at the 5'-end with [$\gamma$-$^{32}$P]ATP using T4 polynucleotide kinase (Sambrook, et al., 1989) with the following modifications. Fifty pmol oligonucleotide, 10 µCi [$\gamma$-$^{32}$P]ATP and 11 units T4 polynucleotide kinase are incubated in reaction buffer for 1 h. labeled probe is purified on Sephadex G-25 spin column. Tetramethyl ammonium chloride (TMAC) is used for hybridization and washes (Ausubel, et at., 1992). Restriction fragments blotted on nylon membrane are prehybridized overnight in 15 ml solution A (5 ml 50× Denhardt's solution, 0.5 ml of denatured salmon sperm DNA 10 mg/ml and 44.5 ml of 5M TMAC) at 42° C. Labeled probe is mixed with 15 ml solution A and hybridized at 54° C. for 1.5 h. Membrane is washed twice for 10 min at room temperature (2× SSC, 0.1% SDS), once for 10 minutes at room temperature (50 mM Tris/HCl, pH 8.0, 3M TMAC, 2 mM EDTA, 0.1% SDS), and the final wash (50 mM Tris/HCl, pH 8.0, 3M TMAC, 2 mM EDTA, 0.1% SDS) for 15 min at 40° C. Membrane is exposed to X-ray film (X-OMAT, Kodak) at −70° C. for 1–3 days. Alternatively, a 5' biotinylated probe and ECL detection system may be used. Such an analysis is shown in FIG. 2.

Oligonucleotide probe design. From a knowledge of the N-terminal amino acid sequence (SEQ ID NO:1) of mutacin, DNA probes may be designed. The following table (Table 7) is included to describe the degeneracy of the nucleic acid code and the means by which the degenerate nucleotide sequence based on the amino acid sequence may be deduced.

TABLE 7

Codon Table

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

DNA-probe hybridization. The [$\gamma$-$^{32}$P]ATP-end labeled degenerate oligonucleotide probe is used to screen for the mutacin structural gene in a library of Tn916-inactivated mutacin-negative (Bac$^-$) mutants (Caufield, et al., 1990B) and their various subclones. To provide certain advantages in accordance with the invention, preferred nucleic acid sequences employed for hybridizations or assays include sequences that are complementary to at least a 10–40 or so nucleotide stretch of degenerate sequences complementary to the amino acid sequences (SEQ ID NOS:1 and 2). A size of at least 10 nucleotides in length helps to insure that the fragment will be of sufficient length to form a duplex molecule that is both stable and selective. Molecules having complementary sequences over stretches greater than 10 bases in length are generally preferred, though, in order to increase stability and selectivity of the hybrid and thereby improve the quality and degree of specific hybrid molecules obtained. Thus, one will generally prefer to design nucleic acid molecules having gene complementary stretches of 15–20 nucleotides or even longer where desired.

Such nucleotide fragments may be readily prepared by, for example, directly synthesizing the fragment by chemical means, by application of nucleic acid reproduction technology such as the PCR technology of U.S. Pat. No. 4,603,102, incorporated herein by reference, or by introducing selected sequencing into recombinant vectors for recombinant production.

Accordingly, the degenerate nucleotide sequences are important for their ability to selectively form duplex molecules with complementary stretches of *S. mutans* mutA gene segments. Depending on the application envisioned, one will desire to employ varying conditions of hybridization to achieve varying degrees of selectivity of the probe toward the target sequence. For applications requiring a high degree of selectivity, one will typically desire to employ relatively stringent conditions to form hybrids, i.e., conditions of high stringency. For example, one will select relatively low salt concentration and/or high temperature conditions such as provided by 0.02 molar to 0.15 molar sodium chloride at temperatures of 50°–70° C. These conditions are particularly selective and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15 molar to 0.9 molar salt at temperatures ranging from 20°–55° C. In any case, it is generally appreciated that conditions can be rendered more stringent by the addition of increasing amounts of formamide which serves to destabilize a hybrid complex in the same manner as increased temperature. Thus hybridization conditions can be easily manipulated and thus will generally be a method of choice depending on the desired results.

EXAMPLE 4

Isolation and Characterization of the Mutacin Gene Loci

The characterization of genes close to the mutacin gene is important in understanding the processes involved in post-translational modification, cleavage and export of mutacin. Identification of this cluster of genes enables specifically directed manipulation of gene sequences so as to affect processing and modification of mutacin properties, perhaps through changes in polypeptide folding.

The combination of insertional inactivation using Tn916 and a reverse genetic approach via purification of mutacin paved the way to construct a degenerative oligonucleotide. This will allow screening of a cosmid library.

The identification of mutacin as a lantibiotic suggests structural and physical analogies to other members of the family, including the well studied antibacterial nisin. Mutacin, like nisin, is genetically encoded and ribosomally transcribed. The polypeptide antibiotic bacitracin, on the other hand, is synthesized by a multi-enzyme complex. Although details of post-translational processing and export for mutacin are as yet undefined, it appears that the genes involved are clustered adjacent to the lantibiotic structural gene. Additional indirect support for the connection between mutacin and nisin comes from the observation that a 23S ribosomal RNA nucleus of *S. mutans* upstream to the bac-1 locus shares striking homology on the order of 90% to the 23S rrn locus of *Lactococcus lactis*, the producer of nisin. A similarity of 90% is perhaps not surprising since rRNA is highly conserved in prokaryotes and since streptococci and lactococci are phylogenetically related. Although the rrn loci of *L. lactis* DL11 are known to be clustered within 20% of the chromosome, the location or relationship between the rrn genes and nisin has not been reported but might be of interest because the bac-1 locus is less than 5 kb away from the one of the 5 rrn loci in *S. mutans* UA96. Moreover, another Tn916-bac-2 cosmid UA33 contains another one of the 23S rrn loci.

Based on the natural competency of *S. mutans* and the 90% homology between the 23S rrn loci of *S. lactis* and *S. mutants*, one can envision the mechanical transfer of the ancestral lantibiotic gene from Lactococcus to *S. mutans* via homologous recombination within the rrn loci flanking the mutacin gene cluster. If transposon elements flanking the mutacin locus are not found (as is the case in lactococcus), this may explain why group II and group I naturally competent strains of *S. mutans* also make mutacin.

Another area for development is the genetic manipulation of the mutacin gene by fusing it to another gene such as a surface antigen recognition protein in a fashion analogous to that which has been done with the *E. coli* colicin and the f1 phage receptor (Jakes, et al., 1988). It is contemplated that one may further direct the specificity of a mutacin by fusing its lethal domain to a *S. mutans* recognition moiety; for example to a monoclonal antibody.

Identification of the genes contiguous or supplemental to the mutacin structural gene. This will be accomplished via "chromosomal walking" to identify segments of DNA directly contiguous with presently cloned mutA sequences. Basic restriction mapping and subcloning will precede DNA sequencing. This initial mapping and sequencing should delineate the coding regions in the mutacin gene cluster involved with mutacin processing and expression. In addition, each of the existing six unique mutacin-negative, Tn916-inactivated mutants will be mapped on the chromosome of UA96 by pulse field gel electrophoresis and Southern hybridization using a Tn916 derived probe. Mutacin-negative Tn916 inserts that are clustered within a fairly defined segment of the genome (~20–30 kb) will be initially selected for more detailed analysis.

Sequencing Genes Contiguous to mutA. Sequencing will be done directly from PCR products as well as from subclones because in the case of Tn916 inserts, for example, one may use outward directed primers to the terminus of Tn916 thus avoiding primer-direct formation because of the redundancy of the LR ends. Any one of several techniques may be used to initiate the PCR reactions, including inverse PCR or ligation-mediated PCR where a primer is added to the ends of a restriction site proximal to the Tn916 insert (<2 kb) (Ochman et at., 1993).

DNA sequencing will employ non-isotope labeling of either primer or dATP with biotin. Chemiluminescent detection is accomplished with a phototype detection kit (New England Biolabs, Beverly, Mass.). Dideoxy chain-termination sequencing is performed by using Sequenase version 2.0 (United States Biochemical, Cleveland, Ohio) in accordance with the manufacturers instructions. Plasmid DNA is isolated either by cesium chloride gradients or alternatively by rapid prep methods, e.g., Insta-prep, 5 Prime->3 Prime, Boulder, Colo. or QIA prep-spin plasmid kit (Quiagene, Chatsworth, Calif.). For denaturation of double-stranded DNA, alkali denaturation followed by annealing with primer at 37° C. for 30 min is used preferably while thermal denaturation is an alternative. Direct blotting sequencer (Hoefer Scientific Instruments, San Francisco, Calif.) will allow resolution of the oligonucleotides (with 300 to 500 bases from sequencing reaction and blotting on nylon membrane in a single step. Radioactive [α-$^{35}$S] ATP sequencing is a common alternative used to resolve sequences in which steric-hindrance of the biotin side chain may cause misreadings. Comparison of obtained sequences with known sequences in DNA data bases will be initially evaluated (DNA Strider software) to map restriction sites and to look for overlaps, secondary structure and other information before transferring the sequence to the Wisconsin Genetics Computer Group (GCG) program for a detailed analysis. Other software programs that may be used include Gene Construction Kit (Textco; W. Lebanon, N.H.) and Oligo 4.0 (National Bioscience, Inc., Plymouth, Minn.).

There are several strategies for identifying relatively large segments of DNA flanking the mutA Locus. The general method of chromosomal walking is readily accomplished by screening a cosmid or lambda library for overlapping sequences. A library of fragments of the appropriate size fragments from chromosomal DNA can be readily made using cosmid cloning techniques. Partial digest with EcoRI and cosmid cloning in vector pJC74 or pJH79 may also be used; however, care must be taken since cosmid packaging can often incorporate non-contiguous fragments and one may wish to employ bacterial alkaline phosphatase (BAP) treatment of ends to limit the joining of non-contiguous segments. *E. coli* libraries containing insert DNA may then be screened. Contiguous fragments will be sub-cloned and analyzed as described. An alternate method of finding contiguous segments of DNA which avoids tedious Southern hybridization involves the insertion of an antibiotic cassette whose phenotype for resistance is expressed in both *S. mutans* and *E. coli*. There exists several candidates for markers (cat, erm, tet, kan) (see Table 8) that could be inserted proximal to mutA, within a suicide vector, and put back into *S. mutans*. A library constructed of flanking segments to mutA could then be surveyed for antibiotic resistance instead of hybridization to a probe to identify the desired clone of cosmid since knockout constructs are contemplated as part of individual gene characterization. One may then use the AB-cassette in an open reading frame (ORF) close to the EcoRI site for this purpose.

Mapping of Tn916 inserts on the UA96 chromosome will allow one to see whether they are found within a discreet cluster or if some of the inserts are in locations other than the putative mutA cluster. Whether the remaining Tn916 inserts lie within a defined cluster is not known and will be determined by using the pulse-field analysis of very large segments of DNA. Some of the Tn916-inserts may not be clustered. However, this does not mean the mutacin associate genes are not clustered. Inserts within general housekeeping genes may yield a Bac$^-$ phenotype yet not be directly involved with mutacin production. As previously stated, all known lantibiotics are products of a contiguous cluster of genes.

The technique of PFGE (pulsed field gel electrophoresis) has been described and used by Tudor and co-workers as part of the mapping of the *S. mutans* GS-5 chromosome (Tudor et al. 1990). In situ lysing of cells of *S. mutans* in agarose blocks precedes restricted digestion with rare base cutters such as SmaI, NotI and others. An almost identical protocol has been employed by Davidson et al. (1991) in mapping the lactis chromosome and by Steen and Hansen (1991). The CHEF-DRIII orthogonal-field apparatus (Bio-Rad) because of its superior generation of patterns facilitating transfer in Southern blotting may be preferred. After transfer of restriction fragments to nitrocellulose membrane via positive pressure blotting Stratagene hybridization to fragments will be accomplished with either biotin labeled or $^{32}$P-ATP-Tn916 probe. Chromosomal DNA from each Bac$^-$ mutant will be included along with a negative control (UA96) and the Tn916 probe which will be a positive control.

Information gained from this series of experiments will indicate the approximate location of each of the Tn916 insert mutants on the chromosome of UA96. Double digestion of chromosomal DNA with more frequent cutters is expected to yield fragments containing several Tn916 inserts for cosmid cloning. Probing of PFGE fragments with mutA will localize that locus relative to other Tn916 inserts. As mentioned previously, it is expected that Bac⁻, Tn916 inserts will be found in locations other than the mutacin-locus. Where there is failure to identify the entire compliment of mutacin genes, PCR and primer to Tn916 will be used for the identification.

Identification of the structure/function of each of the gene products associated with mutacin production. This will be done by sequencing the gene cluster, analyzing the sequence for open reading frames and other characteristics and searching existing data banks for homology with known genes. The gene of interest will then be subcloned onto an appropriate expression vector for determination of gene product using in vitro transcription/translation analysis, mini/maxicell expression in E. coli, or reacted to a panel of polyclonal antibodies made previously to various precursors or components of the mutacin molecule.

The role of each gene in mutacin production will then be examined by constructing a series of either deletion or marker-insertion knockout mutations to determine effects of non-expression. Previously constructed subclones of the entire coding region of the gene of interest within the appropriate expression vector will then be used for complementation assay, keeping in mind gene dosage and regulation may preclude such analysis. One of the goals here is to begin identifying the minimum coding region for mutacin expression so that the entire mutacin cluster may be transferred en bloc to non-mutacin producing strains as has been done with the nisin, epidermin and subtilin lantibiotic clusters.

Once a putative mutacin associated cluster of genes has been identified or if a cluster does not exist, a collection of individually cloned Tn916 containing inserts in cosmids, individual genes in their role and mutacin production will be examined. Initially, various parts of a segment of DNA will be mutagenized in order to narrow down the prospects. One method is to insert AB-cassettes into various restriction sites or to transform with a knockout or suicide plasmid containing smaller fragments of DNA, e.g. pVA891, pMLC19 (Macrina et al. 1983; Nakano and Kuramitsu, 1992) for single cross over integration. The danger with this approach is that upstream insertion of plasmid insert may result in a polar effect of a gene downstream. Given the multi cistronic and coordinate regulation of other lantibiotics, polarity is expected, especially with plasmids containing transcriptional terminators like pVA891. In any event, this approach is expected to lead to information on the mutacin locus as a whole in addition to clues on the role of individual genes.

Sequencing of DNA segments will be initiated based on preliminary information regarding segments thought to be involved with mutacin production. Sequence analysis will reveal open reading frames, restriction sites useful for the construction of knockout mutations, hemolysis with other known sequences and amino acid sequences along with many other attributes.

Characterization of DNA flanking individual Tn916 inserts can be initially performed by PCR using outward directed primers to the right and left ends of Tn916 and either ligated primers or by inverse PCR where Tn916 inserts are cut within flanking segments and then ligated so that the outward directed primers generate a product that crosses the ligated restriction site junction. The limitation here would be the length of the expected PCR product. PCR fragments approaching 5 kb in length can be produced by "long PCR". Smaller fragments less than 2 kb are more readily generated. PCR fragments can be cloned and sequenced or sequenced directly. PCR fragments can also be used as probes to screen a genomic library and a form of inverse PCR can be used for chromosomal walking.

Northern blot analysis and primer extension of mRNA will be used to determine the nature of the mutacin operon (mono and/or polycistronic, putative promoters, post-transcriptional processing of mRNA, stability of transcripts, time in cell cycle of transcripts (mutacin)). Total cellular mRNA will be obtained from wild-type UA96 and separated by size on agarose gels by electrophoresis. A complementary oligonucleotide probe made from the mutA locus and 5 prime and labeled with $^{32}$P-ATP will be used to identify transcripts initially those containing the mutA gene. Oligonucleotide probes will also be made to other sequences within ORF to confirm or identify new transcripts.

Cells of wild type UA96 will be harvested at different time points coinciding with different growth phases and total cellular RNA analyzed by a Northern blot for presence of mutacin transcripts. The intensity of hybridization with label probe will indicate phase in which mutacin transcripts are made. The length of mutacin operon transcripts will be estimated from Northern blots. The putative location of promoters will be accomplished by primer extension using radio-labeled mutA oligoprobe and reverse transcriptase tapes coupled with conventional sequencing using dideoxy termination reaction or PCR primer extension sequencing. This technique will yield the length of transcript as well as its start site. From this information the putative promoter may be deduced from sequence analysis.

The role of the DNA encoding the mutacin gene product, will be examined by introducing deletions or insertional inactivating sequences. The method used will depend to some extent upon the presence of convenient restriction sites such as deletions in the insertions and the ease of scoring successfully made mutations; that is, detection of small deletions may be phenotypically difficult to select for while insertions using antibiotic resistance cassettes may be easier to select and confirm. It will be kept in mind, however, that inserting large segments of inactivating DNA introduces other elements that may affect intervening sequence as well as downstream genes. An approach similar to that used by Hansen (Chung and Hansen, 1992; Liu and Hansen, 1992) for an analysis of the subtilin locus may be employed using a combination of deletion and antibiotic inserts. Basically, the technique involves knowing the DNA sequence and the gene of interest so that a sub-clone may be constructed and an antibiotic cassette (AB-cassette) inserted or segment deleted. The mutation is performed on an E. coli replicon plasmid such as pUC19 only without the Ap$^r$ gene. A recently constructed E. coli medium copy number plasmid pMCL18 and 19 (Nakano and Kuramitsu, 1992) having the p15a derived replicon and Cm$^r$ from pACYC184, the multiple cloning site and ALC1-z from pUC18 to 19 coupled with its successful use in S. mutans makes this construct an ideal vector delivery cassette for making knockout mutants and saturation mutagenesis. Alternatives to pMCL18 and 19 include the gold standard pVA891 (Macrina et al., 1993) which also contains portions of pACYC184. pVA891 lacks the MCS and hence has limited restriction sites for constructing recombinant plasmids. However, the use of PCR by which restriction enzyme tails can be added for compatibility to virtually any site makes this limitation less of a problem. Another potential vector is pKIM2 which also has an MCS and a non β-lactamase gene.

Antibiotic cassettes are readily available and their complete sequences are known, see Table 8. The key feature of AB-cassettes is that they contain the appropriate ribosomal binding site (RBS) and codons for translation and activity in both *E. coli* and *S. mutans*. Potential AB-cassettes include resistance genes to chloramphenicol, erythromycin, kanamycin and tetracycline. Having the availability of multiple AB-cassettes will permit use of several different markers for selection in complementation analysis and confirmation of homologous recombination. Several of these AB-cassettes have been used to inactivate various lantibiotics with some success (e.g. Liu and Hansen, 1992).

TABLE 8

Potential antibiotic resistant cassettes not expressed in *E. coli* and Streptococci.

| AB CASSETTE | ORIGINAL SOURCE | SIZE (KB) | FEATURES | REFERENCE |
| --- | --- | --- | --- | --- |
| erm | *S. pneumoniae*: tn1545 | 1.2 | constitutively expressed | Trieu-Cuot, 1990 |
| kan | *S. faecalis*: pJH1 | 1.5 | aph-3 gene | Trieu-Cuot, 1983 |
| tetO | *S. mutans*: DL5 | 1.9 | complete sequence | LeBlanc, et al., 1988 |
| tetM | *S. faecalis*: tn916 | 2.0 | complete sequence | Burdette, 1990 |
| cat | *S. aureus*: pC194 | 0.8 | complete sequence | Horinouchi and Weisblum, 1992 |

Knowing the sequence of each AB cassette, compatible ends with practically any site within the sequence can be engineered. Also, appropriate ribosomal binding sites, stop codons or other components to enhance expression can be incorporated. It will be preferable to eliminate transcriptional terminators to prevent possible polar effects on downstream genes. The contemplated steps for constructing AB cassette insertional mutans are as follows:

1. Clone the entire or a portion of the gene of interest into the multiple cloning site of pMCL 19.

2. Locate a restriction site, unique if possible, within the cloned insert compatible with the AB cassette because AB cassettes are often contained with the MCS of *E. coli* vectors. A multiple number of restrictions sites are available. If a common restriction site cannot be found, the AB cassette can be amplified by PCR with primers containing tails consistent with any known restriction site. PCR product can then be isolated and ligated into the insert DNA. Successful recombinants can be selected by expression of the AB cassette.

3. Linearize plasmids containing the inserts, AB cassettes from *E. coli* and transform into *S. mutans* UA 96. By homologous recombination, double cross-over exchange followed by expression of AB phenotype, transformants having the AB insert can be readily selected ($10^{-6}$–$10^{-7}$ transformants per recipient). These can be screened for the mutacin phenotype. Southern blot will be used to confirm size and location of each insert.

Using this basic approach, a series of insertional inactivated mutants can be constructed. Additionally, the entire gene cloned for complementation analysis will be used to determine whether the sequence acts in cis or is a soluble gene product acting in trans. The drawback here is that the gene of interest must have an appropriate flanking promoter and terminator together with appropriate gene dosage and regulation. Given that most genes associated with known lantibiotics do not have their own promoters or transcriptional terminators, it is likely that these will need to be added to inserted Streptococci replicons before complementation can be anticipated. This can be done by using PCR primers having these coding sequences. Complementation has been previously achieved using vector pVA 838 and the entire 12 kb bac-1, EcoRI insert.

Although the composition and size of the gene product from each mutacin associated gene can be protected from DNA sequence analysis, it is possible by analogy with the nisin protein that the gene product undergoes posttranslational modification. Therefore, an in vitro transcription and translation system will be employed. This system is straightforward, using $^{35}$S-methionine or one of several other amino acids as the marker for proteins synthesized in vitro. Both plasmid DNA and linear DNA fragments can be translated with this system in instances when the protein is absent or processed. $^3$H-leucine may also be used to achieve labelling. Reaction mixtures can be concentrated with 5% TCA prior to treatment with SDS if low abundance or low molecular weight proteins are expected. Samples may be separated on SDS-PAGE gels and labelled proteins visualized by autoradiography.

The in vitro method is simple and requires less time or preparation than mini or maxi cell systems. Also, the gene products are expressed in vitro, lessening the problems with gene product lethality or cell memory and damage to the cell producing mutacins. The transcription-translation system has been used successfully to examine gene products from pPC313, so it is clear that at least some *S. mutans* genes are expressed in this system. It is important to note that results from this assay may not be definite in terms of size of the gene product, particularly if the mutacin gene is post-translationally processed. Post-translational processing and modifications are anticipated. Therefore, comparison of gene products will be made with those in a Streptococci system having the necessary processing enzymes. Mini or maxi cells can be used for gene product analysis as well.

Proteins or peptides made in vitro can be compared to those made in situ by a mutacin producer. Polyclonal antibodies can be made against peptides or proteins cut out of a polyacrylamide gel confirmed by Western immunoblot analysis then used in subsequent experiments to identify a localization of each gene product of mutacin processing. This approach has been successfully employed to localize nisP and nisR gene products within the membrane of *Lactococcus lactis* (van der Meer, et al. 1993.) Various cell fractions can be run in separate lanes in both denaturing and nondenaturing polyacrylamide gels and their reaction to specific antisera observed (Western blot).

The above information will allow one to define the minimal necessary coding sequence for en bloc transfer of the mutacin locus to a nonproducer. En bloc transfer of nisin, epidermin and subtilin loci has been accomplished. As previously discussed, several competent non-mutacin producing strains of *Streptococcus mutans* are available, including UA 130, UA 159 and GS 5. It will also be determined whether the competent group I, mutacin I strains can be transformed to mutacin II strains. Under species transfer of the mutacin locus would be of interest, particularly if oral Streptococci such as *S. sanguis* could be converted to produce mutacin. Such a construct might constitute a viable effector strain capable of excluding the colonization of *S. mutants* from the oral cavity. *S. sanguis* has been shown to colonize infants at 12 months while *S. mutans* colonizes around 24 months. Plasmid borne or chromosomal inserts of the mutacin locus could be accomplished given the ability to introduce a construct into the host. Gene dosage and regulation of mutacin would be a factor in determining how the construct would be delivered and sustained in the new host. Electroporation techniques exist for transforming many of the oral and non-oral Streptococci. See, for example, Genetics and Molecular Biology of Streptococci, Lactococci and Enterococci, 1991, ASM.

EXAMPLE 5

Production of Anti-Mutacin Antibodies

In another aspect, the present invention contemplates an antibody that is immunoreactive with the mutacin polypeptide of the invention. An antibody can be a polyclonal or a monoclonal antibody. In a preferred embodiment, an antibody is a monoclonal antibody. Means for preparing and characterizing antibodies are well known in the art (please see, e.g., Antibodies "A Laboratory Manual, E. Howell and D. Lane, Cold Spring Harbor Laboratory, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for the mutacin of the present invention may be prepared using conventional immunization techniques, as will be generally known to those of skill in the art. A composition containing antigenic epitopes of the mutacin can be used to immunize one or more experimental animals, such as a rabbit or mouse, which will then proceed to produce specific antibodies against the purified mutacin polypeptide. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with an antigenic mutacin polypeptide composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the mutacin polypeptide of the present invention.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against mutacin. Hybridomas which produce monoclonal antibodies to the selected antigens are identified using standard techniques, such as ELISA and Western blot methods.

Preparation of monoclonal antibodies. Balb/c mice of approximately 3 months in age are immunized intraperitoneally (day 0) with 10 to 50 μg/mouse of the purified mutacin polypeptide homogenized Complete Freunds Adjuvant. The mice are given two to five consecutive intraperitoneal injections every 10 to 14 days of the antigens mixed with Incomplete Freunds Adjuvant. Approximately one month after the final injection, a booster inoculation of antigen in phosphate buffered saline is given intravenously into the tail vain.

Five to 7 days after the booster injection, a small amount of blood from the tail of the immunized mice is removed and tested for the presence of circulating antibodies to mutacin by an enzyme-linked immunosorbent assay (ELISA). Those mice producing reasonable titers of circulating antibodies to the partially purified antigens are sacrificed and their spleens will be aseptically removed for cell fusion.

The mouse myeloma cell line proposed to be of use for hybridization is the 8-azaguanine-resistant mouse murine myeloma SP2/0 non-producer cell line. The SP2/0 cell line has been selected for 8-azaguanine resistance and does not survive in medium containing hypoxanthine, aminopterin, and thymidine (HAT). The cells are fused as described in (Chan et al., 1987). Immune splenocytes ($10^8$ cells) obtained from hyperimmunized mice and 8-azaguanine-resistant SP2/0 mouse myeloma cells ($10^7$ cells) are fused using 37% (w/v) polyethylene glycol 1500 (M.W. 500–600 M.A. Bioproducts, Inc.). Fused cells are maintained for two days in growth medium that has been conditioned by SP2/0 cells, and then plated in five or six 96-well microtiter plates in growth medium containing HAT (selection medium) and screened for antibody production at the end of 2 weeks by indirect ELISA.

For the screening, purified mutacin or partially purified mutacin obtained from the T8 Streptococcus mutans strain are used as target antigens, and non-producing bacteria are used as a control. The target antigens (50 ng/50 μl/well) may be immobilized onto the bottoms of the 96-well microtiter plates by incubating in carbonate buffer pH 8.8 at 4° C. overnight. The culture medium from the wells propagating the splenocyte-myeloma (hybridoma) cells growing in the selection medium may be assayed for secreted antibodies that react with the immobilized antigens. The isotypes of the immunoglobulin(s) produced by cloned hybridoma cell clones may also be determined by ELISA, employing a commercial isotyping kit. The specificity of the mAbs may be determined by their reactivity with various antigens, as examined by ELISA and confirmed by western blot analysis.

After the mAbs are characterized, they may be produced in the form of mouse ascites fluid, purified and used to detect mutacin production, inhibit mutacin action, Western blotting analysis, immunoprecipitation, diagnostic identification of mutacin producing Streptococci or for the purification of mutacin. This assay is proposed to be a reproducible, convenient and rapid assay method.

Hybridoma clones can then be cultured in liquid media and the culture supernatants purified to provide the anti-mutacin specific monoclonal antibodies. It is proposed that the monoclonal antibodies of the present invention will find useful application in standard immunochemical procedures, such as ELISA and Western blot methods, as well as other procedures which may utilize antibody specific to mutacin epitopes.

Additionally, it is proposed that monoclonal antibodies specific to the particular mutacin may be utilized in other useful applications. For example, their use in immunoabsorbent protocols may be useful in purifying native or recombinant mutacin from other species or variants thereof.

In general, both poly- and monoclonal antibodies against mutacin polypeptide antigens may be used in a variety of embodiments. For example, they may be employed in antibody cloning protocols to obtain cDNAs or genes encoding other mutacin or related proteins. They may also be used in inhibition studies to analyze the effects of Streptococcal infection and mutacin production in cells or animals. Antimutacin antibodies will also be useful in immunolocalization studies to analyze the distribution of intracellular mutacin during various cellular events, for example, to determine the production and distribution of the mutacin polypeptide during the presence or absence of propitious growth conditions. A particularly useful application of such antibodies is in purifying native or recombinant mutacin, for example, using an antibody affinity column. The operation of all such immunological techniques will be known to those of skill in the art in light of the present disclosure.

EXAMPLE 6

Modify the Mutacin Molecule Via Its DNA Coding Sequence to Enhance Antimicrobial Or Physical Properties A method of preparing variants of the S. mutans mutacin polypeptide is site directed mutagenesis. This technique is useful in the preparation of individual peptides or biologically functional equivalent proteins or peptides derived from the 2.5 kDa protein sequence through specific mutagenesis of the underlying DNA. The technique further provides a ready ability to prepare and test sequence variance, for example, incorporating one or more of the foregoing considerations by introducing one or more nucleotide sequence changes into the DNA. Site directed mutagenesis allows the production of mutants through the use of specific oligonucleotide sequences which encode the DNA sequence of the desired mutation as well as a sufficient number of adjacent nucleotides to provide a primer sequence of sufficient size and sequence complexity to form a stable duplex on both sides of the deletion junction being traversed. Typically a primer of about 17–25 nucleotides in length is preferred with about 5–10 residues on both sides of the junction of the sequence being altered.

In general, the technique of site specific mutagenesis is well known in the art as exemplified by publications (Adelman, et al., 1982). As will be appreciated, the technique typically employs a phage vector which exists in both a single stranded and double stranded form. Typical vectors useful in site directed mutagenesis include vectors such as the M13 phage (Messing, et al., 1981). These phages are readily commercially available, and their use is generally well known to those skilled in the art.

Site directed mutagenesis in accordance herewith is performed by first obtaining a single stranded vector which includes within its sequence a DNA sequence which encodes a mutacin DNA polypeptide. An oligonucleotide primer bearing the desired mutated sequences prepared, generally synthetically, for example, by the method of Crea, et al. (1978). This primer is then annealed with the single stranded vector and subjected to DNA polymerizing enzymes such as E. coli polymerase I Klenow fragment in order to complete the synthesis of the mutation bearing strand. Thus the heteroduplex is formed wherein one strands encodes the original non-mutated sequence, and the second strand bears the desired mutation. This heteroduplex is then used to transform appropriate cells such as E. coli cells, and clones are selected which include recombinant vectors bearing the mutated sequence arrangement.

The preparation of sequence variances of the selected mutA S. mutans gene using site directed mutagenesis is provided as a means of producing potentially useful and improved mutacin polypeptides and is not meant to be limiting as there are other ways in which sequence variance of the mutA gene may be obtained. For example, recombinant vectors encoding the desired gene may be treated with mutagenic agents to obtain sequence variance for the mutagenesis of plasmid DNA using hydroxyl amine.

This will be accomplished by combination of cassette saturated mutagenesis and a finer targeted site-directed mutagenesis. Prior to mutagenesis, however, a detailed understanding of the chemical and genetic properties of the mutacin molecule will be obtained. The DNA sequences of mutacin will be compared to mutA locus. Mutacin I is a closely related mutacin with a slightly different range of activity. Differences in sequence are likely to provide clues as to where to modify the sequence to produce a wider spectrum molecule.

Chemical analyses by NMR and mass spectroscopy of the polypeptide will allow detection of modified amino acid residues (e.g., didehydrobutyric acid or didehydroalanine), thioether bridges and spatial configuration of the molecule. Genetic analyses deduced from DNA sequence data in combination with chemical analyses will yield information about hydrophobic/hydrophilic domains, antigenicity, amphipathic configuration and charge distribution. This information, along with comparisons to other well-studied lantibiotics will assist in the design of site-directed mutagenesis for modification of the mutacin peptide.

While site directed mutagenesis has been widely used, the technique presumes certain information concerning the target site which is to be mutagenized. Thus, in the case of subtilin, (Liu and Hansen, 1992) a specific amino acid, glutamine, at position 4 was changed to isoleucine. Apparently, the carboxyl group of glutamine destabilized the adjacent didehydrolalanine causing a decrease in the biological half-life of the subtilin molecule. A single substitution of Ile for Glu increased the half-life of subtilin 57 fold. This remarkable enhancement of the subtilin molecule points to the possibility that other modifications of this and other lantibiotics may endow the molecules with enhanced antimicrobial properties.

The mutagenesis approach seems attractive because S. mutans UA96 is naturally competent and the peptide mutacin is relatively small. Also by being able to introduce mutated sequences into the chromosome of S. mutans, gene dosage and regulation are maintained, in contrast to using a plasmid replicon to produce the mutated product. Other clues as to what areas of the mutagenesis to modify may come from available strains of S. mutans that produce mutacin. One, is a closely related mutacin made by Group I S. mutans with a slightly different spectrum of activity and physical properties (Caufield, et al., 1985).

Initially, it is proposed to start with a more or less random mutagenic approach called saturation cassette mutagenesis (Bedwell and Strobel, 1989; Hill, et al. 1987). An approach similar to that of Liu and Hansen (1992) will be employed with the following modifications. The vector for cloning and delivering the modifying mutacin gene will be pMCL 19. Plasmid MCL has the Cat gene and MCS from pUC19. An Erm AB cassette will be inserted into the structural gene of mutacin as described once the exact sequence is known. This will indicate whether or not homologous exchange has taken place. The structural gene mutA will also be cloned into pMCL 19. In addition, a tetO or kan AB cassette will be inserted distal to the mutacin gene at a site that does not alter activity or processing of the mutacin antibiotic. Certain trial and error insertions are necessary here but with the aid of PCR custom inserts can be made to fit unique restriction sites. Included in the mutacin insert will be downstream sequences of approximately 50 base pairs which will serve as homologous regions for reciprocal exchange.

The system will be tested by linearizing the pNCL19 chimera and transform UA96. Selection for Erm$^s$ Tet$^r$ should yield transformants that underwent homologous exchange. Screening for mutacins should be positive. Southern blots should confirm a single insert at the appropriate location.

Oligonucleotides of approximately 50 to 100 bp in length will be synthesized based upon the sequence of mutA. Degeneracy will be built in at each first and second nucleotide of each codon. The wild-type nucleotide will be added to the oligo-synthesizing reaction along with the remaining three mutagenic nucleotides in a ratio of approximately 33:1 to 1:1. The first approximation of this ratio is based upon the Poisson calculation so that a given degenerative oligonucleotide will have just one point mutation. The ratio will be determined based upon the length of the final mutA sequence and the outcome will be tested empirically. Two degenerative oligos of approximately 50 to 90 bp whose sequence was derived from the left and right ends of the approximately 100 bp mutA and having a 10 to 20 bp overlap will be synthesized. Areas of overlap will be used to prime the Klenow polymerase and double stranded DNA fragment will result that can be ligated into the pMCL delivery factor. Sites for ligation will be predetermined from mutA locus sequence data. The unique sites can be engineered into non-essential sequences by site directed mutagenesis. PCR can also be used to extend the overlapping sequences. The oligos can also be designed to have terminal design recognition sites to aid in the directional cloning of the insert; for example, PstI and HindIII.

Ligated inserts derived from a series of oligonucleotides containing more or less random substitutions will be delivered by a linearized suicide vector, pMCL19, and transformants its having the Tet$^r$ Erm$^s$ phenotype will be screened for antimicrobial activity or other desired properties. The DNA sequence of promising mutations can be obtained and mapped to delineate the various regions of the mutacin molecule responsible for a particular phenotype, for example, antimicrobial spectrum of activity. The tet or kan AB cassette will facilitate recovery of the chromosomally located mutated insert.

Confirmation of curative changes in codons will consist of amino acid composition in sequence analysis. Proton NMR spectrum analysis has proven useful in determining structural changes in the subtilin molecule. Altered mutacins molecules can be recovered by methods similar to those used for recovering wild type mutacin.

EXAMPLE 7

Enhanced Production of Mutacin

One of the problems with antibiotics isolated from natural sources is low yields and extensive purification processes. The following example illustrates a strategy for overproducing mutacin from a bacterial host, employing DNA constructs to transform gram positive bacterial cells. While gram-negative bacteria, typically E. coli are generally employed as expression systems, other strains which lack the outer membrane of gram-negative bacteria such as B. subtilis, L. lactis or S. sanguis are expected to provide enhanced yields.

Further aspects of the invention include high expression vectors incorporating DNA encoding the new mutacin and its variants. It is contemplated that vectors providing enhanced expression of mutacin in systems other than S. mutans will be obtainable. E. coli high expression vectors such as the T7 expression system in E. coli are not likely to process and export mutacin correctly, because the gram negative cell with its outer membrane will likely lack many or all of the mutacin processing enzymes. Moreover, even en bloc transfer of all mutacin processing genes to the E. coli system will probably not yield active mutacin. However, other gram-positive microorganisms am expected to be suitable options, particularly, for example, B. subtilis which has been employed to produce subtilin. In addition to the B. subtilis, the inventors contemplate that other species of streptococci such as S. sanguis or lactococci will also prove to be suitable expression hosts.

Expression systems for large scale production or enhanced expression in S. mutans or other host systems. Modifications of the physical properties of mutacin may be sought that increase its solubility or expression in liquid culture. The mutacin locus may be placed under control of a high expression promoter or the S. mutans system regulation altered to enhance expression.

Scaling up from a 20-liter tank to 1,000-liter or more will be based on parallel analysis of mutacin production (bioassay and/or reverse phase HPLC), expression of mutacin specific proteins and genes (Northern and Western blots, SDS-PAGE) and correlated with nutrient levels at different stages of scale-up. Physiological studies should reveal major control mechanisms for mutacin production. Isolation and purification of mutacin from 20 to 1,000 liters would depend on production range, but generally the following steps would be performed:

1. Liquid containing mutacin will be separated from cells. Filtration (Pellicon filter system, Millipore, 0.45 µm membrane) or centrifugation could be used.

2. Isolation and concentration of mutacin. Two ultrafiltration steps (Pellicon filter system, Millipore, ultrafiltration membranes) using a 10 kDa ultrafiltrate and 1 or 2 kDa retentate should be sufficient. Alternatively, adsorption on adsorber resins or cation exchange chromatography could be used.

3. Selective liquid extraction/precipitation might be used before application of reverse phase HPLC for final purification. This might be followed by lyophilization or chemical modification (to change activity or increase solubility).

4. Lyophilization.

The purification scheme should meet the criteria for clinical and pre-clinical investigations, i.e., product purity higher than 99%, ability to purify large amounts of peptide at pilot scale over 50% overall yield and to achieve cost effectiveness.

Fermentation processes in isolation of proteins from fermentation broth after cultivation of S. mutans are known. Pellicon cassette separator (Millipore, Bedford, Mass.) allows fast separation of cells from a liquid (HVLP cassette, 0.45 µm). The application of pellicon filter separator will be analogous to small scale isolation procedures by the Minitan separator (Millipore, Bedford, Mass.) previously described. The use of 10 kDa and 1 kDa pellicon membranes will enable collection of mutacin in a 1 kDa retentate (minimum volume using Pellicon filter system is 250–750 ml, depending on the type of pump. Possible filtration rates for Pellicon filter systems with rotary vein pumps allows one to obtain 1.5 to 150 liters of filtrate per hour. Because mutacin is thermostable, there is no special need for fast purification or extra caution in the separation conditions. Heat denaturation in the purification step is also a possibility. All heat labile proteins should be denatured and discarded as a pellet after centrifugation. Then the next steps of ultrafiltration should proceed at a higher speed and yield pure substance. The crude mutacin will be further processed directly. The final purification of mutacin will be performed by reverse phase HPLC, the usual modern method for purifications with over 99% purity. For some purposes, selective precipitation from solution (8M urea, 70% ethanol, for example) by 20-fold excess of water may be sufficient. For further analysis of purified mutacin and modified mutacins, it may be necessary to use size exclusion chromatography combined with amino acid analysis, for example, to track purification.

Mutacin production and purification is also contemplated to be accomplished by the combination of overproduction of unprocessed pre-protomutacin (protein with leader peptide before modification) in a heterologous host followed by its modification on a column with immobilized modification enzymes. The effluence in the column would contain highly purified active substance. Cell extracts containing the processing enzymes for nisin combined with the pre-nisin peptide have resulted in the production of active nisin (van der Meer, 1993).

Spectroscopic studies used to elucidate the primary structure of bio-active metabolites will include the use of NMR and mass spectroscopy as well as fast atom bombardment mass spectroscopy (FAB-MS). This knowledge, together with known amino acid composition, will be used in MS study of tryptic peptides isolated by reverse phase HPLC and other cleaved peptides. For example, CNBr digestion should yield two peptides because of the presence of one methionine residue in the mutacin primary structure. This technique has been successfully used in studies of epidermin. An alternative possibility is direct mutacin sequencing by FAB-MS. Structural sub-units of mutacin could be established by proton NMR and $^{13}$C NMR, the standard initial approach in determining the structure of a novel component. Involvement of chemical modifications or shorter peptide analysis and/or extension NMR analysis including deuterium NMR measurements might open the way to NMR studies of mutacin conformation in solution.

EXAMPLE 8

Large Scale Screening of *Streptococcus* Mutants

The following example indicates that two different mechanisms operate by which the Tn916 transposon inserts into the recipient chromosome in naturally competent strains of *S. mutans*. The effect of a resident helper plasmid on the frequency of Tn916 inserted transformants has also been demonstrated. These differences in transformation frequencies become critical if a particular mutation is sought and a large number of transformants are required for screening.

Transpositional Mutagenesis Using Tn916 in *S. mutans*. *S. mutans* UA96 was transformed using two different Tn916 containing plasmids. Plasmid pAM118 was constructed from vector pVA838 and contain the streptococcal replicon from *S. ferrus* pVA380-1 in addition to Tn916. Plasmid pAM620 was similar except it lacked the streptococcal replicon and thus was unable to replicate in *S. mutans*. When *S. mutans* UA96 was first transformed with these two Tn916 containing plasmids, differences in numbers of transformants and colony morphologies were observed. Specifically, the non-replicative pAM620 yielded wild type (WT) transformants which were yellow, raised and had a typical mutans colony morphology while the transformants arising from the replicative plasmid pAM118 were small white colonies. On primary plates (Todd-Hewitt with 5 mg/ml tetracycline) the different colony morphs were distinct and readily identified; on secondary isolation after several days growth, small white colonies became WT morphologies. Because pAM118 gave 20 times more transformants than pAM620, this difference was exploited so more mutants could be produced per transformation. Freshly prepared plasmid DNA gave higher transformation rates than month-old or older preparation. This was likely the result of the inherent instability of the CCC-form of the Tn916 intermediate. Primary Tet$^r$ transformants from both colony morphologies were then screened for resistance to both Tet and Erm; the small whites were both Tet$^r$ Erm$^r$ while the WT from pAM620 were Tet$^r$ Erm$^s$. Since vector PVA38 carries the Erm gene, it was deduced that the small whites had acquired the Erm$^r$ from plasmid pVA838. pVA838 could either be integrated into the chromosome itself of UA96 or recircularized to form a replicating plasmid in UA96. Plasmid screening showed that indeed a plasmid consistent with pAM118 left a 16.4 kb Tn916 was incorporated in the small white transformants.

Transformants arising from the non-replicative pAM620 were the likely result of transformation by the CCC-intermediate. To confirm that the small whites arose from a replicative plasmid and WT morphs rose from the CCC-intermediate, advantage was taken of the fact that linearized plasmid DNA could not transform *S. mutans* unless by homologous recombination with a chromosome or homology with a resident plasmid.

Plasmid pAM118 and pAM620 were linearized with restriction enzymes KpnI which cuts once within the Tn916 but not within vectors pVA838 or PVA891 and XbaI which cuts within vectors but not within Tn916. If the transforming moiety in all cases had been the Tn916 intermediate transforming plasmid preparations of pAM620 and pAM118 cut with XbaI would transform Tn916 not linearized and preps cut with KpnI would not transform *S. mutans* because KpnI cuts within the intermediate. The results of this experiment are shown in Table 9.

TABLE 9

Transformation frequencies for *S. mutans* UA96 transformed with Tn916-containing plasmid pAM118 linearized with different restriction enzymes.

| Restriction endonuclease | WT Yellow | Small, white |
|---|---|---|
| None | 2.3 | 45.0 |
| XbaI | 0.7 | 0 |
| KpnI | 0 | 0 |

In the case of transformation by a non-replicative plasmid such as pAM620, Tn916 intermediate forms a CCC-intermediate in the *E. coli* host from which the preparation is derived, prior to transformation. It is this intermediate that is the transforming moiety responsible for Tet$^r$ transformants. This is evident by the absence of transformants when the transforming DNA is cut with KpnI which linearizes the intermediate and the plasmid pAM118 as well. Cutting pAM118 with XbaI linearizes the plasmid pAM118 but does not linearize Tn916 intermediate formed in *E. coli*. Hence, WT transformants at a reduced frequency arise. This experiment also showed that the WT colonies arose from the Tn916 intermediate whereas the small whites arose from the replicating plasmid where transposition is a secondary event after the Tn916-containing replicative plasmid pAM118 enters and becomes established in the transformed *S. mutans*.

This result indicated that two mechanisms were involved because: (1) WT colony transformants arose from the Tn916 intermediate, and (2) its agreement with the earlier observations (Gawron-Burke and Clewell, 1984) of the so-called "zygotic induction" of a transforming plasmid. These two

41 conflicting hypotheses are reconciled by the observation that the transformation of *S. gordonii* and *S. mutans* are similar in that both occur by natural competence and both involve the uptake of single stranded DNA. Hence, in order for a plasmid to become established, it requires the entry of two partially overlapping plasmid molecules of DNA by so-called two-hit kinetics.

Anything that would stabilize or foster the formation of plasmid DNA in mutants would also increase the transformation rate as a result of a secondary zygotically induced event occurring after the plasmid DNA entered the cell and became established. This would result in small white colony transformants as seen with replicates of plasmid pAM118. *S. mutans* was then transformed with the parent plasmid of pAM118, pVA38, transformed and the resulting strain transformed with Tn916-containing plasmids pAM620 and pAM118. The results are shown in Table 10.

TABLE 10

| | Transformation Rate[a] × $10^6$ for colony type | | |
|---|---|---|---|
| Donor Plasmid | Helper[b] | WT | Small, whites |
| pAM118 | – | 1.7 | 41 |
| | + | 1.0 | 720.0 |
| pAM620 | – | 3.1 | 0 |
| | + | 1.5 | 37.0 |

[a] transformation frequency = # transformants/total no. cells at $t_o$
[b] Helper plasmid pVA838

The number of Tet[r] transformants arising from the replicate of plasmid pAM118 were nearly 20-fold higher than that of non-helper recipients. Tet[r] transformants arising from the non-replicative plasmid pAM620 were comparable to non-resident helper negative recipients, 1.7 and 3.1 for pAM118 and pAM620, respectively, demonstrating that the establishment of a replicative plasmid containing Tn916 was a prerequisite for secondary excision, i.e., zygotic induction, of Tn916 and insertion into the chromosome of *S. mutans*. Small white colony transformants arose from pAM620. These transformants were the result of recombination between the income pAM620-containing vector pVA891 and the resident pVA838, the parent vector of pVA891. This was further support that Tet[r] transformants arose as a secondary transposition from the plasmid to the chromosome in *S. mutans*. In screening *S. mutans* transformants for DNA in this or previous experiments, no plasmids were observed that were consistent in size with the original pAM118 indicating that Tn916-containing plasmid is unstable in *S. mutans*. The small white colony morphology appears to be the result of transient carriage of the Tn916 plasmid causing the cell to grow more slowly. Subcultures of small white morphs presumably arising after transposition has occurred revert to WT colony morphology.

Competition experiments were then conducted whereby chromosomal or plasmid DNA of differing amounts were co-transformed with pAM620 or pAM118. Homologous chromosomal DNA having a streptomycin resistance marker competed with Tn916 transformants showing that chromosomal DNA, Tn916-intermediate and Tn916-containing plasmids enter and transform *S. mutans* by common pathway.

The importance of this observation of two different mechanisms for involving the Tn916 intermediate and the secondary transpositional event from a replicating plasmid is that Tn916 inactivated mutants can be generated at a rate on the order of $10^{-3}$ to $10^{-4}$ transformants/recipient compared to the rate of $10^{-5}$ first observed. This difference in transformation frequencies becomes critical as particular mutations are sought.

EXAMPLE 9

Transformation of Bacterial Strains

Certain strains of *Streptococcus mutans* are not naturally competent. The efficacy of transformation depends on the strain transformed, the cultural conditions and the nature of the transforming DNA. In this example, it is shown how cultural conditions were manipulated to increase the transformation rates of *S. mutans*.

Transformation of *S. mutans*. The transformation rates for two naturally occurring competent serotype C strains were compared. One strained harbored a 5.6 kb plasmid UA96 and the other was plasmid-free (T8). These strains were compared to widely used strain GS5. All three strains exhibited enhanced transformation frequencies between 6- and 150-fold when bovine serum albumin was substituted for horse serum and chemically defined medium substituted for Todd-Hewitt medium.

Overall, strain UA96 exhibited the greatest rate of transformation in CDM supplemented with 0.4% BSA showing a 40- to 152-fold increase for plasmid and chromosomal DNA respectively. In spite of UA96 which possesses a more favorable transformation rate, T8 was chosen for further study because it lacked the resident plasmid 5.6 kb which is found in UA96. The presence of this resident plasmid complicates the genetic characterization of plasmid constructs of interest introduced into competent cells because both resident and chimeric plasmid co-purify in $CsCl_2$ gradient centrifugation. The relationship between time of incubation, culture density and transformation rate of T8 in CDM enriched with 0.4% BSA using pVA838 as the transforming moiety.

The time interval between 1 to 6 hours of incubation demonstrated a sharp rise and fall in competence as measured by the rate of transformation with an optimum at 3 hours. The maximum rate of transformation coincided with the end of the lag phase with a rapid decline preceding the exponential growth phase. The rapid decline in competence corresponded to the junction between the lag and exponential growth curve. A similar pattern occurred with both TS5 and UA96, suggesting that the maximal transformation rate correlates to the lag phase of growth and falling sharply at the beginning of the exponential growth phase.

Although *S. pneumoniae* and some group H streptococci attained various degrees of competence in a serum or albumin free medium, the mutans streptococci tested attained competence only in the presence of serum derived components. It is not clear how serum derived additives promote competence. The ability to enhance transformation of *S. mutans* using CDM enriched with 0.4% BSA has an additional advantage in allowing determination of what other substances, if any, are involved with the development of competence in this organism. The absence of multiple polypeptides in CDM compared with a complex medium such as TH is another advantage, making isolation purification of expressed polypeptides much less cumbersome. In addition, the use of CDM opens the way for further elucidation of extracellular components involved with natural competence in *S. mutans*.

EXAMPLE 10

Effect of recA On Mutacin Expression

Certain other bacteriocins such as the colicins from *E. coli* are recA dependent. This prompted investigation of the effect of a recA mutant on the expression of mutacin in *S. mutans*. The recA gene is responsible for the coating of the recA protein. This is a highly conserved regulator of homologous recombination DNA repair and proteolytic activation of the "SOS" pathway. A recA mutation in the mutacin strain UA96 using PCR amplification was constructed. Primers were made directly to the conserved regions of recA from *E. coli* and *B. subtilis*. The experiment was designed to study the effect of recA disruption on mutacin production and transformation ability in *S. mutans*.

Role of the recA mutation on mutacin production and transformation. Oligonucleotide primers from conserved regions of the recA loci from both *E. coli* and *B. subtilis* were used as primers for PCR amplification. EcoRI "tails" were added and the PCR internal fragment of recA cloned into shuttle plasmid pVA891 (Erm$^r$Cm$^r$). This chimera was used as the transforming DNA for the homologous chromosomal recombination. Because pVA891 is unable to replicate in *S. mutans*, only those integrating into chromosome yield Erm$^r$ transformants. Transformations were performed using this construct as a donor in both UA96 and its isogenic strain T8, which lacks the 5.6 kb plasmid.

Profound differences in UV sensitivities were observed in the Bac$^-$ mutants compared with its parent strain. UV sensitivity is one of the phenotypic expressions of incomplete DNA repair. Erm$^r$ transformants were four orders of magnitude more sensitive to UV irradiation than the parent strain. Using internal recA as a probe for Southern blot of two independently isolated Erm$^r$ mutants confirmed that the insertions were in the same restriction fragment. Transformation frequencies in the putative recA mutants for both plasmid DNA and chromosomal DNA were below detection at less than $10^{-7}$. However, no differences were seen in the production of mutacin between the mutant and parent strains. Collectively, these results indicated that the recA gene in *S. mutans* strains UA96 and T8 were inactivated and responsible for both UV sensitivity and decrease in competence. However, it is not related to mutacin production.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Allgaier, H., G. Jung, R. G. Werner, U. Schneider, and H. Zähner. 1985. Elucidation of the structure of epidermin, a ribosomally synthesized tetracyclic heterodetic polypeptide antibiotic. Angew. Chemie. 24:1051–1053.

Allgaier, H., G. Jung, R. G. Werner, U. Schneider, and H. Zähner. 1986. Epidermin: sequencing of a heterodetic tetracyclic 21-peptide amide antibiotic. Eur. J. Biochem. 160:9–22.

Augustin, J., R. Rosenstein, B. Wieland, U. Schneider, N. Schnell, G. Engelke, K. Entian, and F. Gotz. 1992. Genetic analysis of epiderm biosynthetic genes and epidermin-negative mutants of *Staphylococcus epidermidis*. Eur. J. Biochem. 204:1149–1154.

Ausubel, F. M., R. Brent, R. E. Kingston, D. D. Moore, J. G. Seidman, J. A. Smith, and K. Struhl. 1992. Current protocols in molecular biology, p. In (ed.), Greene Publishing Associates and Wiley-Interscience, New York.

Bedwell, D. and S. Strobel. 1989. Sequence and structural requirements of a mitochondrial protein import signal defined by saturation cassette mutagenesis. Mol. Cell. Biol. 9:1014–1025.

Booth, M. C. and Gilmore, M. 1993. Expression of component A of the *Enterococcus faecalis* cytolysin by transposon insertion mutants. Amer. Soc. Microbiol. 93:Abstract #B217.

Buchman, G. W., S. Banerge, and J. N. Hansen. 1988. Structure, expression, and evolution of a gene encoding the precursor of nisin, a small protein antibiotic. J. Biol. Chem. 263:16260–16266.

Burdett, V. 1990. Nucleotide sequence of the tet(M) gene of Tn916. Nucl. Acid Res. 18:6137.

Caufield, P. W., G. Shah, S. K. Hollingshead, M. Parrot, and M. C. Lavoie. 1990A. Evidence that mutacin II production is not mediated by a 5.6-kb plasmid in *Streptococcus mutans*. Plasmid 24:110–8.

Caufield, P. W., G. R. Shah, and S. K. Hollingshead. 1990B. Use of transposon Tn916 to inactivate and isolate a mutacin-associated gene from *Streptococcus mutans*. Infect. Immun. 58:4126–35.

Caufield, P. W., N. K. Childers, D. N. Allen, and J. B. Hansen. 1985. Distinct bacteriocin groups correlate with different groups of *Streptococcus mutans* plasmids. Infect. Immun. 48:51–56.

Chou and Fasman. 1974a. Prediction of protein conformation. Biochemistry. 13(2):222–245.

Chou and Fasman. 1974b. Conformational parameters for amino acids in helical, β-Sheet, and random coil regions calculated from proteins. Biochemistry. 13(2):211–222.

Chou and Fasman. 1978a. Prediction of the secondary structure of proteins from their amino acid sequence. Adv. Enzymol. Relat. Areas Mol. Biol. 47:45–148.

Chou and Fasman. 1978b. Empirical predictions of protein conformation. Ann. Rev. Biochem. 47:251–276.

Chou and Fasman. 1979. Prediction of β-Turns. Biophys. J. 26:367–384.

Chung, Y. and J. N. Hansen. 1992. Determination of the sequence of spaE and identification of a promoter in the subtilin (spa) operon in *Bacillus subtilis*. J. Bacteriol. 174:6699–6702.

Davidson, B. E., L. Finch, D. Tulloch, R. Llanos, and A. Hillier. 1991. Physical and genetic mapping of the *Lactococcus lactis* chromosome, p. 103–108. In G. Dunny, P. Cleary, and L. McKay (ed.), Genetics and Molecular Biology of Streptococci, Lactococci and Enterococci., American Society for Microbiology, Washington D.C.

Delisle, A. L. 1986. Properties of mutacin b, an antibacterial substance produced by *Streptococcus mutans* strain BHT. Microbios, 46:21–28.

Dodd, H. M., N. Horn, and M. J. Gasson. 1990. Analysis of the genetic determinant for production of the peptide antibiotic nisin. J. Gen. Microbiol. 136:555–566.

Fetrow & Bryant. 1993. New programs for protein tertiary structure prediction. BIOTECHNOLOGY. 11:479–483.

Gawron-Burke, C. and D. B. Clewell. 1984. Regeneration of insertionally inactivated streptococcal DNA fragments after excision of transposon Tn916 in *Escherichia coli*: Strategy for targeting and cloning of genes from gram-positive bacteria. J. Bacteriol. 159:214–21.

Gross, E. and H. Kiltz. 1973. The number and nature of α,β-unsaturated amino acids in subtilin. Biochem. Biophys. Res. Commun. 50:559–565.

Gross, E. and J. L. Morell. 1971. The structure of nisin. J. Am. Chem. Soc. 93:4634–4635.

Hamada, S., H. Imanishi, and T. Ooshima. 1986. Isolation and mode of action of a cell-free bacteriocin (mutacin)

from serotype g *Streptococcus mutans* MT3791. Zentralbl. Bakteriol. Mikrobiol. Hyg. [a]. 261:287–98.

Hill, D. E., A. R. Oliphant, and K. Struhl. 1987. Mutagenesis with degenerated oligonucleotides: and efficient method for saturating a defined DNA region with base pair substitutions. Meth. Enzymol. 155:558–568.

Hopp. U.S. Pat. No. 4,554,101.

Horinouchi, S. and B. Weisblum. 1982. Nucleotide sequence and functional map of pC194, a plasmid that specifies inducible chloramphenicol resistance. J. Bacteriol. 150:815–825.

Horn, N., S. Swindell, H. Dodd, and M. Gasson. 1991. Nisin biosynthesis genes are encoded by a novel conjugative transposon. Mol. Gen. Genet. 128:129–135.

Howell, E. and D. Lane. 1988. Antibodies "A Laboratory Manual, Cold Spring Harbor Laboratory, New York.

Howell, T. H. and J. P. Fiorellini. 1993. The effect of a mouthrinse based on nisin, a bacteriocin, on developing plaque and gingivitis in beagle dogs. J. Clin. Periodont. 20:335–339.

Hurst, A. 1981. Nisin. p. 85–123. In Advances in applied microbiology 1981. Academic Press.

Jakes, K. S., N. G. Davis, and N. D. Zinder. 1988. A hybrid toxin from bacteriophage f1 attachment protein and colicin E3 has altered cell receptor specificity. J. Bacteriol. 170:4231–4238.

Jameson and Wolf. 1988. The antigenic index: a novel algorithm for predicting antigenic determinants. Comput. Appl. Biosci. 4(1):181–186.

Jung, G. 1991. Lantibiotics: a survey, p. 1–34. In G. Jung and H. Sahl (ed.), Nisin and other novel lantibiotics, ESCOM Science Publishers, Leiden.

Kaletta, C., and K.-D. Entian. 1989. Nisin, a peptide antibiotic: cloning and sequencing of the nisA gene and posttranslational processing of its peptide product. J. Bacteriol. 171:1597–1601.

Kaletta, C., K.-D. Entian, R. Kellner, G. Jung, M. Reis, and H.-S. Sahl. 1989. Pep5, a new lantibiotic: structural gene isolation and polypeptide sequence. Arch. Microbiol. 152:16–19.

Kyte, J. and Doolittle, R. F. 1982. A simple method for displaying the hydropathic character of a protein. J. Mol. Biol. 157(1):105–132.

LeBlanc D. J., L. Lee, B. Titmas, C. Smith, and F. Tenover. 1988. Nucleotide sequence analysis of tetracycline resistance gene tetO from *Streptococcus mutans* DL5. J. Bacteriol. 170:3618–3626.

Liu, W. and J. N. Hansen. 1991. Conversion of *Bacillus subtilis* 168 to a subtilin producer by competence transformation. J. Bacteriol. 173:7387–7390.

Liu, W. and J. N. Hansen. 1992. Enhancement of the chemical and antimicrobial properties of subtilin by site directed mutagenesis. J. Biol. Chem. 267:25078–25087.

Loyola, R. J. P., I. Morisaki, K. Kitamura, and S. Hamada. 1992. Purification and properties of extracellular mutacin, a bacteriocin from *Streptococcus sobrinus*. J Gen Microbiol. 138:269–274.

Macrina, F., R. P. Evans, J. A. Tobian, D. L. Hartley, D. B. Clewell, and K. R. Jones. 1983. Novel shuttle plasmid vehicles for Escherichia-Streptococcus transgeneric cloning. Gene. 25:145–150.

Macrina, F. L., J. L. Reider, S. S. Virgili, and D. J. Kopecko. 1977. Survey of the extrachromosomal gene pool of *Streptococcus mutans*. Infect Immun. 17:215–26.

Messing et al. 1981. Third Cleveland Symposium on Macromolecules and Recombinant DNA. Editor A. Walton, Elsevier, Amsterdam.

Miller, E. J., D. K. Furuto, and A. J. Narkates. 1991. Quantitation of type I, III, and V collagens in human tissue samples by high-performance liquid chromatography of selected cyanogen bromide peptides. Anal. Biochem. 196:54–60.

Miller, E. J., A. J. Narkates, and M. A. Niemann. 1990. Amino acid analysis of collagen hydrolysates by reverse-phase high-performance liquid chromatography of 9-fluorenylmethyl chloroformate derivatives. Anal. Biochem. 190:92–97.

Nakano, Y. J. and H. K. Kuramitsu. 1992. Mechanism of *Streptococcus mutans* glucosyltransferases: hybrid-enzyme analysis. J. Bacteriol. 174:5639–46.

Ochman, H J., F. Ayala, and D. Hartl. 1993. Use of polymerase chain reaction to amplify segments outside boundaries of know sequences. Method. Enzymol. 218:309–321.

Parrot, M., P. W. Caufield, and M. C. Lavoie. 1990. Preliminary characterization of four bacteriocins from *Streptococcus mutans*. Can J Microbiol. 36:123–30.

Pinto A. M., M., Zelante, F. Guidolin, R. 1992. Isolation of Mutacins in Cell Free Extracts and Analyses of Some Physical and Biologic Properties. Rev. Microbiol., Sao Paulo. 23(4):221–225.

Sahl. H. 1991. Pore formation in bacterial membranes by cationic lantibiotics., p. 347–358. In Nisin and other novel lantibiotics, G. Jung and H. Sahl, (ed.), 1991, ESCOM Science Publishers: Leiden.

Sambrook, J., et al. (1989), Molecular Cloning: A Laboratory Manual, Cold Spring Harbor Laboratory, Cold Spring Harbor, N.Y.

Schnell, N., G. Engelke, J. Augustin, R. Rosenstein, F. Gotz, and K. Entian. 1992. Analysis of genes involved in the biosynthesis of lanthionine epidermin. Eur. J. Biochem. 204:57–68.

Sevag, M. G., D. Lackman, and J. Smolens. 1938. The Isolation of the Components of Streptococcal Nucleo Proteins and Serologically Active Form. J. Biol. Chem. 124:425–436.

Shah, G. R., J. Novak, P. W. Caufield, and K. F. Dybvig. 1993. Effect of recA on mutacin production and competence in *S. mutans*. J. Dent. Res. 72:155.

Steen, M. and J. N. Hansen. 1991. Structure, expression, and evolution of the nisin gene locus in *Lactococcus lactis*, p. In Genetics and molecular biology of Streptococci, Lactococci and Enterococci, G. Dunny, P. Cleary, and L. McKay, (ed.), 1991, Amer. Soc. Microbiol.: Washington, D.C.

Steen, M. T., Y. J. Chung, and J. N. Hansen. 1991. Characterization of the nisin gene as part of a polycistronic operon in the chromosome of *Lactococcus lactis* ATCC 11454. Appl. Environ. Microbiol. 57:1181–1188.

Tagg, J. R., A. S. Dajani, and L. W. Wannamaker. 1976. Bacteriocins of gram-positive bacteria. Bacteriol. Rev. 40:722–756.

Tagg, J. R., N. L. Ragland, and N. P. Dickson. 1990. A longitudinal study of Lancefield group A streptococcus acquisitions by a group of young Dunedin schoolchildren. N. Z. Med. J. 103:429–31.

Trieu-Cuot, P. and P. Courvalin. 1983. Nucleotide sequence of the *Streptococcus faecalis* plasmid gene encoding the 3'5"-aminoglycoside phosphotransferase type III. Gene. 1983:331–341.

Trieu-Cuot, P., C. Poyart-Salmeron, C. Carlier, and P. Courvalin. 1990. Nucleotide sequence of the erythromycin resistance gene of the conjugative transposon Tn1545. Nuc. Acid Res. 18:3660.

Tudor, J., L. Marri, P. J. Piggot, and L. Moore. 1990. Size of the *Streptococcus mutans* GS-5 chromosome as determined by pulsed-field gel electrophoresis. Infect. Immun. 58:838–840.

van der Meer, J. R., J. Polman, M. M. Beerthuyzen, R. J. Siezen, O. P. Kuipers, and W. M. de Vos. 1993. Characterization of the *Lactococcus lactis* nisin A operon genes nisP, encoding a subtilisin-like serine protease involved in precursor processing and nisR, encoding a regulatory protein involved in nisin biosynthesis. J. Bacteriol. 175:2578–2588.

van der Rijn, I. and R. E. Kessler. 1980. Growth Characteristics of a Group A Streptococci in a new chemically defined media. Infect. Immunol. 27:444–448.

Wolf et al.. 1988. An integrated family of amino acid sequence analysis programs. Comput. Appl. Biosci. 4(1):187–191.

What is claimed is:

1. An isolated DNA segment comprising a nucleic acid sequence encoding a polypeptide comprising the amino acid sequence of SEQ ID NO:1 wherein said polypeptide has the following properties:

(a) antibacterial activity against gram positive microorganisms;

(b) a $M_r$ of about 2,500 as determined by size exclusion gel chromatography and SDS-PAGE; and (c) an amino acid composition comprising the following amino acids per molecule; $Arg_2$, $Asp_2$, $Glu_3$, Gly, His, Ile, Lys, Met, Pro, $Trp_2$, Tyr, $Val_3$, $Xaa_2$, Yaa;

wherein Xaa represents lanthionine and Yaa represents β-methyllanthionine.

2. The DNA segment of claim 1, further defined as encoding a polypeptide which includes the amino acid sequence Met Asn Xaa Xaa Trp His Xaa (SEQ ID NO:2), where the Xaa is independently lanthionine or β-methyllanthionine.

3. A recombinant vector comprising a DNA segment in accordance with claim 1.

4. A recombinant host cell comprising a recombinant vector in accordance with claim 3.

5. The recombinant host cell of claim 4, wherein the host cell is *S. mutants, E. coli, S. cerevisae, Bacillus sp., Lactococci sp., Enterococci sp.,* or *Salmonella sp.*

6. The recombinant host cell of claim 5, further defined as a host cell having a recA phenotype.

7. A recombinant vector comprising a DNA segment which comprises a nucleotide sequence encoding the amino acid sequence of SEQ ID.NO:2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 8 amino acid residues
        ( B ) TYPE: amino acid
        ( C ) STRANDEDNESS: single
        ( D ) TOPOLOGY: linear ( i x ) SEQUENCE DESCRIPTION: SEQ ID NO:1:
        Asn Arg Trp Trp Gln Gly Val Val
        1                     5

( 2 ) INFORMATION FOR SEQ ID NO:2:

( i ) SEQUENCE CHARACTERISTICS:
        ( A ) LENGTH: 7 amino acid residues
        ( B ) TYPE: amino acids
        ( C ) STRANDEDNESS: single
        ( D ) TOPOLOGY: linear ( i x ) SEQUENCE DESCRIPTION: SEQ ID NO:2:
        Met Asn Xaa Xaa Trp His Xaa
        1                 5